US011634699B2

(12) United States Patent
Clubb et al.

(10) Patent No.: US 11,634,699 B2
(45) Date of Patent: Apr. 25, 2023

(54) REAGENT TO LABEL PROTEINS VIA LYSINE ISOPEPTIDE BONDS

(71) Applicants: The Regents of the University of California, Oakland, CA (US); The Board of Regents of The University of Texas System, Austin, TX (US)

(72) Inventors: Robert T. Clubb, Culver City, CA (US); Brendan Rayhan Amer, Los Angeles, CA (US); Janine Y. Fu, Rancho Palos Verdes, CA (US); Scott McConnell, Los Angeles, CA (US); Hung Ton-That, Manvel, TX (US); Chungyu Chang, Seabrook, TX (US)

(73) Assignees: THE REGENTS OF THE UNIVERSITY OF CALIFORNIA, Oakland, CA (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 16 days.

(21) Appl. No.: 17/052,116

(22) PCT Filed: May 1, 2019

(86) PCT No.: PCT/US2019/030206
§ 371 (c)(1),
(2) Date: Oct. 30, 2020

(87) PCT Pub. No.: WO2019/213262
PCT Pub. Date: Nov. 7, 2019

(65) Prior Publication Data

US 2021/0115424 A1 Apr. 22, 2021

Related U.S. Application Data

(60) Provisional application No. 62/665,076, filed on May 1, 2018.

(51) Int. Cl.

| | |
|---|---|
| ***C12N 9/52*** | (2006.01) |
| ***C07K 1/13*** | (2006.01) |
| ***C12P 21/00*** | (2006.01) |

(52) U.S. Cl.
CPC .................. *C12N 9/52* (2013.01); *C07K 1/13* (2013.01); *C12P 21/00* (2013.01)

(58) Field of Classification Search
CPC ............ C12N 9/52; C07K 1/13; C07K 19/00; C07K 2319/02; C07K 2319/21; C07K 2319/50; C12P 21/00; C12Y 304/22; C12R 2001/16; C12R 2001/445
See application file for complete search history.

(56) References Cited

U.S. PATENT DOCUMENTS

| | | | |
|---|---|---|---|
| 2003/0022178 A1 | 1/2003 | Schneewind et al. |
| 2004/0029129 A1 | 2/2004 | Wang et al. |
| 2017/0226495 A1 | 8/2017 | Guimaraes et al. |

OTHER PUBLICATIONS

Ton-That, "Assembly of pili on the surface of *Corynebacterium diphtheriae*". Molecular Microbiology, vol. 50, Issue 4, Nov. 2003. <URL: https://onlinelibrary.wiley.com/doi/full/10.1046/j.1365-2958.2003.03782.x> (Year: 2003).*

Spirig, "Sortase enzymes in Gram-positive bacteria". Molecular Microbiology, vol. 82, Issue 5, Dec. 2011. <URL: https://onlinelibrary.wiley.com/doi/10.1111/j.1365-2958.2011.07887.x> (Year: 2011).*

Kang, Hae Joo, et al. "The *Corynebacterium diphtheriae* shaft pilin SpaA is built of tandem Ig-like modules with stabilizing isopeptide and disulfide bonds." Proceedings of the National Academy of Sciences 106.40 (2009): 16967-16971. (Year: 2009).*

Guttilla, Irene K., et al. "Acyl enzyme intermediates in sortase-catalyzed pilus morphogenesis in gram-positive bacteria." Journal of bacteriology 191.18 (2009): 5603-5612. (Year: 2009).*

Yanai, Ryoji M.D., Ph.D.; Ueda, Kiichi M.D., Ph.D.; Nishida, Teruo M.D., D.Sc.; Toyohara, Megumi M.S.; Mori, Osamu M.S.. Effects of Tonicity-Adjusting and Surfactant Agents on the Antimicrobial Activity of Alexidine. Eye & Contact Lens: Science & Clinical Practice: Mar. 2011—vol. 37—Issue 2 (Year: 2011).*

Bellucci, Joseph J., Jayanta Bhattacharyya, and Ashutosh Chilkoti. "A noncanonical function of sortase enables site-specific conjugation of small molecules to lysine residues in proteins." Angewandte Chemie 127.2 (2015): 451-455. (Year: 2015).*

Jacobitz, Alex W., et al. "The "lid" in the *Streptococcus pneumoniae* SrtC1 sortase adopts a rigid structure that regulates substrate access to the active site." The Journal of Physical Chemistry B 120.33 (2016): 8302-8312. (Year: 2016).*

Thermo Fisher Scientific Fluorophore Selection, https://www.thermofisher.com/us/en/home/life-science/cell-analysis/fluorophores.html, accessed Aug. 10, 2022 (Year: 2022).*

(Continued)

*Primary Examiner* — Louise W Humphrey
*Assistant Examiner* — Candice Lee Swift
(74) *Attorney, Agent, or Firm* — Gates & Cooper LLP

(57) ABSTRACT

Covalently cross-linked pilus polymers displayed on the cell surface of Gram-positive bacteria are assembled by class C sortase enzymes. These pilus-specific transpeptidases located on the bacterial membrane catalyze a two-step protein ligation reaction—first, cleaving the LPXTG motif of one pilin protomer to form an acyl-enzyme intermediate, and second, joining the terminal threonine to the nucleophilic lysine residue residing within the pilin motif of another pilin protomer. Informed by the high-resolution crystal structures of corynebacterial pilus-specific sortase (SrtA) and by developing structural variants of the sortase enzyme whose catalytic pocket has been unmasked by activating mutations, we have developed new reagents capable of forming isopeptide bonds in vitro. The reagents disclosed herein can catalyze ligation of isolated SpaA domains in vitro provide a facile and versatile new platform for protein engineering and bio-conjugation that has major implications for biotechnology.

10 Claims, 17 Drawing Sheets

Specification includes a Sequence Listing.

(56) References Cited

OTHER PUBLICATIONS

PCT International Search Report & Written Opinion dated Sep. 17, 2019 for PCT Application No. PCT/US2019/030206.

Yu, F, "Generating Affinity Proteins for Biotechnological, Diagnostic and Therapeutic Applications". Thesis paper [online]. Royal Institute of Technology, School of Biotechnology, Stockholm. 2015, 99 pages.

Chang, G et al., "In Vitro Reconstitution of Sortase-Catalyzed Pilus Polymerization Reveals Structural Elements Involved in Pilin Crosslinking. Proceedings of the National Academy of Sciences of the U.S.A". Jun. 12, 2018, Epub May 29, 2018, vol. 115, No. 24; pp. E5477-E5486.

McConnell, Sa et al., "Protein Labeling via a Specific Lysine-Isopeptide Bond Using the Pilin Polymerizing Sortase from *Corynebacterium diphtheriae*". Journal of the American Chemical Society. Jul. 11, 2018, Epub Jun. 28, 2018, vol. 140, No. 27; pp. 8420-8423.

* cited by examiner

REAGENT TO LABEL PROTEINS VIA LYSINE ISOPEPTIDE BONDS

CROSS REFERENCE TO RELATED APPLICATIONS

This application is the National Stage of International Application No. PCT/US19/30206 (International Publication No. WO 2019/213262), filed May 1, 2019, which claims the benefit under 35 U.S.C. Section 119(e) of commonly-assigned U.S. Provisional Patent Application Ser. No. 62/665,076, filed on May 1, 2018, and entitled "REAGENT TO LABEL PROTEINS VIA LYSINE ISOPEPTIDE BONDS" which application is incorporated by reference herein.

STATEMENT AS TO RIGHTS TO INVENTIONS MADE UNDER FEDERALLY SPONSORED RESEARCH AND DEVELOPMENT

This invention was made with government support under Grant Number DE017382/DE025015, awarded by the National Institutes of Health and DE-FC02-02ER63421 awarded by the U.S. Department of Energy. The government has certain rights in the invention.

TECHNICAL FIELD

This disclosure relates to methods and materials useful for forming isopeptide bonds.

BACKGROUND OF THE INVENTION

Reagents that site-specifically conjugate various molecules (e.g. peptides, drugs, detectable agents and the like) to polypeptides such as proteins have a wide range of potential uses, including among others: the construction of antibody-drug conjugates (ADCs) to treat disease, selective domain labeling for biophysical studies, the construction of immuno-PET reagents for non-invasive imaging, cell specific labeling, and the preparation of multifunctional protein nanoparticles and complexes for industrial purposes. Currently, the sortase A enzyme from *Staphylococcus aureus* (Sa-SrtA) is perhaps the most widely used bioconjugation reagent. Sa-SrtA is used in the art to generate antibody conjugates, nucleic acid-protein fusions, PEGylation/lipidated proteins, live cell-labeling, protein cyclization, silent labeling, domain labelling, to add proteins to solid supports, and the like.

While conventional Sa-SrtA is a useful bioconjugation reagent, it can only attach molecules to the C- or N-terminus of a protein via a backbone peptide bond. In this context, it would be highly desirable to have new reagents and associated methods that allow artisans to conjugate polypeptide side chains via isopeptide bonds because in principle, this will enable any surface on a polypeptide to be modified. In addition, such linkages are less susceptible to proteolysis and, therefore provide this advantage over other peptide bonds.

For the reasons noted above, there is a need in the art for methods and materials useful for forming isopeptide bonds, for example in methods of site-specific protein modification and engineering.

SUMMARY OF THE INVENTION

As discussed in detail below, we have developed new enzyme reagents that are capable of coupling polypeptides together via the formation of isopeptide bonds, as well as a variety of methodologies for using such reagents. The new enzyme reagents comprise bacterial Class C sortase variant polypeptides having one or more amino acid mutations in the lid region of the sortases, mutations that unexpectedly confer the enzymes with an ability to catalyze threonine-lysine isopeptide bond formation in vitro. The new sortase enzymatic activity disclosed herein can be adapted for use in a wide variety of conventional methodologies that are used in the art to modify polypeptides such as proteins.

The new methods and materials disclosed herein are useful, for example, in applications of the type which conventionally use *Staphylococcus aureus* Sortase A (Sa-SrtA), a transpeptidase that has been widely adopted for site-specific protein modification and engineering, but which only allows for the formation of new amide bonds between a C-terminal sorting motif LPXTG (SEQ ID NO: 5 where X equals any amino acid) and an N-terminal oligoglycine. The key difference between such conventional reagents and the invention is that the new enzymatic reagents disclosed herein can create isopeptide bonds, not peptide bonds. In this context, there are a number of advantages to attaching polypeptides together via isopeptide bonds. These advantages include enabling new sites on polypeptides to be labeled (as Sa-SrtA is only efficient at modifying N- and C-termini). In addition, these new enzymatic reagents can be used in combination with conventional Sa-SrtA in order to enable multiple molecules to be attached to a single protein (e.g. antibody-drug conjugates that contain both a drug as well as a label for tracking tissue distribution). The invention technology disclosed herein can be used in a wide variety of contexts, for example to generate antibody conjugates, nucleic acid-protein fusions, PEGylation/lipidated proteins, live cell-labeling, protein cyclization, silent labeling, domain labeling, to add proteins to solid supports etc. etc. In addition to providing new ways to couple polypeptides together, this isopeptide linkage activity is further desirable because the modification is specific, and the isopeptide linkages may be less susceptible to proteolysis than conventional peptide bonds.

As discussed in detail below, it has been discovered that introducing amino acid mutations (e.g. substitutions and deletions) into the lid region of Class C bacterial sortases can provide these enzymes with a new activity, namely an ability to form isopeptide linkages between a threonine residue in a first polypeptide and a lysine residue in a second polypeptide. Certain working embodiments of the invention disclosed herein utilize an active truncated variant *Corynebacterium diphtheriae* sortase (SEQ ID NO. 1) having substitution and/or deletion mutations in the lid region of a Cd-SrtA polypeptide. In this context, embodiments of the invention include compositions of matter comprising a variant polypeptide having at least 90% identity to a *Corynebacterium diphtheriae* Class C sortase polypeptide (e.g. SEQ ID NO. 1, SEQ ID NO. 40 or SEQ ID NO. 41), wherein the *Corynebacterium diphtheriae* Class C sortase variant polypeptide comprises at least one amino acid substitution mutation or deletion in the lid region of the polypeptide; and the *Corynebacterium diphtheriae* Class C sortase variant polypeptide exhibits an increased ability to catalyze threonine-lysine isopeptide bond formation in vitro as compared to wild type *Corynebacterium diphtheriae* Class C sortase.

Typically in the compositions of the invention, the variant polypeptide comprises at least two substitution or deletion mutations in the lid region of the *Corynebacterium diphtheriae* Class C sortase, for example those selected from the group consisting of D45, W47 and N49 of SEQ ID NO: 1.

In certain embodiments of the invention, the variant polypeptide comprises substitution mutations D45G and W47G in SEQ ID NO: 1, and optionally a further substitution mutation in SEQ ID NO: 1 such as N49A. In other embodiments of the invention, the variant polypeptide comprises a deletion mutation in at least one amino acid of residues 43-51 of SEQ ID NO: 1. Optionally, the *Corynebacterium diphtheriae* Class C sortase variant polypeptide in such compositions exhibits an ability to form isopeptide bonds in vitro that is at least 25% or 50% of the ability to form isopeptide bonds exhibited by a *Corynebacterium diphtheriae* sortase polypeptide comprising lid region substitution mutations D45G and W47G in the polypeptide of SEQ ID NO: 1 or lid region deletion mutations in amino acids 43-51 the polypeptide of SEQ ID NO: 1.

The compositions of the invention include those used in the methods of the invention discussed below and can include additional reagents pertinent to such methods. For example, in certain embodiments of the invention, compositions can further comprise at least one of a polypeptide (e.g. a polypeptide comprises an amino acid sequence YPKN (SEQ ID NO. 6) or LPLT (SEQ ID NO. 7)), a polynucleotide, a lipid, a sugar, a therapeutic agent or a detectable label. In certain embodiments of the invention, the polypeptide, the polynucleotide, the lipid, the sugar, the therapeutic agent or the detectable label is coupled to a polypeptide comprising an amino acid sequence YPKN (SEQ ID NO. 6) or LPLT (SEQ ID NO. 7). In some embodiments of the invention, the compositions further include a wild type Class C sortase bacterial polypeptide such as a *Staphylococcus aureus* sortase polypeptide (e.g. SEQ ID NO: 2).

Other embodiments of the invention methods of forming an isopeptide bond in vitro between a threonine residue in a first polypeptide and a lysine residue in a second polypeptide, the method comprising forming a mixture comprising the first polypeptide and the second polypeptide disposed within a bacterial Class C sortase variant polypeptide composition such as those disclosed herein (e.g. using a composition discussed immediately above); and then allowing the sortase variant polypeptide to form an isopeptide bond between the threonine residue in the first polypeptide and the lysine residue in the second polypeptide, so that an isopeptide bond between a threonine residue in a first polypeptide and a lysine residue in a second polypeptide is formed. In certain embodiments of the invention, the methods include using a polypeptide having an amino acid motif comprising at least four contiguous amino acid residues that is present in a SpaA (SEQ ID NO: 3) or a SpaB (SEQ ID NO: 4) polypeptide (e.g. the amino acid motif LPXT (SEQ ID NO: 8)). Optionally, an agent used in such methods comprises a detectable marker (e.g. a fluorophore or a PET label), an antibody, a growth factor or a fluorescent protein. Such methodological embodiments of the invention can be used in a wide variety of common biotechniques including therapeutic agent-polypeptide conjugation, nucleic acid-polypeptide conjugation, detectable marker-polypeptide conjugation, PEGylation or lipidation of proteins, detectably labelling live cells, protein cyclization, silent labeling, domain labeling, covalently attaching polypeptides to solid supports and the like.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIGS. 1A-1E: Structural analysis of the *C. diphtheriae* pillus-specific sortase SrtA—FIG. 1(A) The crystal structure of SrtA was determined to 2.1-Å resolution, with the overall protein fold presented as rainbow coloring from blue to red corresponding to the N- to C-terminal positions; the helices are marked as H1-H7 and the β-strands β1-β8. FIG. 1(B) The WT lid region is marked in red with conserved lid residues D81 and W83 and catalytic residues C222, H160 and R231 in yellow. Cys222 residue is shown only in the main conformation. FIG. 1(E) Superposition of the $SrtA^{WT}$ (green) and the lid mutant $SrtA^{2M}$ (pink) structures was generated by PyMOL.

FIG. 3(B) In vitro reconstitution of SpaA pilus polymerization was carried out at room temperature using various forms of recombinant SrtA and SpaA proteins at the molar ratio of 1:3. The reaction samples were analyzed by SDS-PAGE and Coomassie staining after 0, 24 h, and 48 h of incubation. Additional samples with 72 h of incubation were taken for the $SrtA^{2M}$ reactions (black triangles). SpaA monomers (M), polymers, (P) and molecular weight markers are indicated. A SrtA-SpaA intermediate is marked with asterisks. FIG. 3(C) Protein samples from pilus polymerization reactions were analyzed by electron microscopy with negative staining using 1% uranyl formate. For comparison, recombinant $SrtA^{2M}$ (right panel) and SpaA-K190A (left panel) proteins were included. FIG. 3(D) The isopeptide bond from between the residue T494 of the LPLTG (SEQ ID NO. 5) motif and the lysine residue K190 of the pilin motif in SpaA polymers in (B) was examined by tandem mass spectrometry. Shown is the mass-to-charge ratio (m/z) tandem mass spectrum of the linked peptide (sequence shown in the inset). FIG. 3(E) Fusion proteins between SUMO and the N-terminal SpaA domain ($^{N}$SpaA; residues 30 to 194) and between maltose-binding protein MBP and the C-terminal SpaA domain ($^{C}$SpaA; residues 350 to 500) were used with the $SrtA^{2M}$ enzyme in the in vitro pilus polymerization assay as described in (B). The reaction samples were analyzed by SDS-PAGE and Coomassie staining after 24 h. The reactive lysine K190 and the LPXTG (SEQ ID NO: 5) motif in the two domains are indicated.

FIG. 4(A) A SrtA-SpaA pilin polymerase attack complex was visualized and assembled using PyMol. Shown is a SpaA molecule splitting into its two domains, $^{N}$SpaA (light blue) and $^{C}$SpaA (dark blue). The SrtA enzyme is shown in green, and the H1-helix potentially bridging interactions between the two SpaA domains is seen in orange. FIG. 4(B) The detailed locations of the SrtA catalytic triad (marked in yellow) and the surrounding residues at the active site of the pilin polymerase attack complex are shown. The N-terminal H1 helix bridges the two reactive domains of SpaA and potentially facilitates the interactions for formation of the SrtA-SpaA polymerization attack complex. FIG. 4(C) Transpeptidation activity of SrtA2M and its variants (N165A, Y225A, N228A, and S229A) was determined in the pilus polymerization assay described in FIG. 3E, using domain substrates $^{N}$SpaA and $^{C}$SpaA. Protein samples were analyzed by SDS-PAGE and Coomassie staining after 24 h. Ligated product $^{C}$SpaA-$^{N}$SpaA, sortase enzymes, substrates, and molecular markers are indicated. FIG. 4(D) Hydrolysis activity of SrtA enzymes was determined by an HPLC-based assay. 50 μM SrtA (wild-type or mutants) was incubated with 500 μM KNAGFELPLTGGSGRI (SpaApep) (SEQ ID NO: 9) in a 100 μl assay at 37° C. for 48 h. Reaction products were monitored and separated using HPLC at absorbance of 215 nm. The peak fractions were collected and identified by MALDI-TOF mass spectrometry. The hydrolysis activity by SrtA$^{2M}$ is set as 100%. The results were presented as average of three independent experiments.

FIG. 8(A) Structure of CdSrtA$^{WT}$ showing the inhibitory "lid" (blue). Side chains that were mutated to activate the enzyme are shown as yellow sticks. The surface of the catalytic site is colored red. FIG. 8(B) Protein-protein ligation using the activated CdSrtA$^{3M}$ enzyme. SDS-PAGE analysis of the reaction demonstrating formation of the lysine-isopeptide linked $^{N}$SpaAx$^{C}$SpaA product. The reaction (100 μM enzyme, 300 μM $^{C}$SpaA and $^{N}$SpaA) was sampled at 0, 24 and 48 hours. FIG. 8(C) High yield protein-peptide labeling with CdSrtA$^{3M}$. MALDI-MS data showing that >95% $^{N}$SpaA is labeled with peptide containing the sort-tag, LPLTGpeptide (KNAGFELPLTGGSGRI (SEQ ID NO. 9)). MS spectra recorded at 0 (black) and 24h (grey) are overlayed. FIG. 8(D) ESI MS/MS data confirming that the peptide attached to the protein in panel (C) is covalently joined via a specific lysine-isopeptide linkage between K190 and the threonine residue in the peptide.

FIG. 9(A) Schematic showing CdSrtA$^{3M}$ catalyzed labeling of pilin motif (PM) fusion protein with a peptide that contains the LPLTG sorting signal and a functional label. FIG. 9(B) SDS-PAGE analysis of a fluoropeptide modification reaction containing CdSrtA$^{3M}$ (100 μM) and FITC-KNAGFELPLTGGSGRI (SEQ ID NO. 9) (1 mM) and either $^{N}$SpaA (lanes 1-3) or $^{N}$SpaA(K190A) (lanes 4-6) (both 100 μM). Top and bottom panels are the same gels visualized by fluorescence or by coomassie staining, respectively. Reaction progress was measured at 0 (lanes 1,4), 24 (lanes 2,5) and 48 hrs (lanes 3,6). FIG. 9(C) Protein-protein ligation with CdSrtA$^{3M}$. As in panel (B), except reactions contained GFP-LPLTG (SEQ ID NO. 5) (300 μM) instead of the fluoropeptide. Reactants were visualized with coomassie staining at 0, 24 and 48 hrs (lanes 1-3, respectively).

FIG. 10(A) Sequential reaction scheme used to install fluorogenic peptides on a target protein via peptide- and isopeptide-bonds. G5-SUMOPM is a SUMO target protein that is fused to N- and C-terminal nucleophiles, pentaglycine (G5) and the pilin motif, respectively. FIG. 10(B) SDS-PAGE analysis of reaction components taken at different steps in the procedure. 1) prior to labeling, 2) after labeling with FITC-LPLTGpep using CdSrtA$^{3M}$ and 3) after attaching the A546-LPATG using SaSrtA (0.25/2 hr labeling times). Panels show as indicated fluorescence gel imaging to detect FITC and A546 fluorophores using 488/530 and 532/605 nm wavelengths for excitation/emission, respectively, and the merged image of the gels demonstrating dual labeling. FIG. 10(C) As in panel B except the proteins were visualized by coomassie staining and the molecular weight ladder is included.

FIG. 11(A) The three CdSrtA mutants tested demonstrate differential transpeptidation activities upon incubation with SpaA pilin domains. Each CdSrtA mutant (WT, D81G/W83G, D81G/W83G/N85A) was incubated with $^{N}$SpaA and $^{C}$SpaA for 24 and 48 hours, and the reactions were separated by SDS-PAGE. Notably, the WT construct has negligible transpeptidation activity in vitro, presumably because of substrate occlusion from the active site by the lid structure. FIG. 11(B) Quantification of the relative amounts of $^{N}$SpaA-$^{C}$SpaA isopeptide-linked dimer produced was determined by densitometry analysis of the gel images in ImageJ2. Densitometry values for all reactions were plotted as factor of the transpeptidation product formed by CdSrtA$^{WT}$ after 24 hrs. FIG. 11(C) Peptide hydrolysis data indicates CdSrtA$^{3M}$ forms acylation product faster than the other mutants tested. Cleavage and acylation of the cell wall sorting signal peptide is the first step of sortase catalysis. Each CdSrtA construct was incubated with a 10× molar excess of LPLTG (SEQ ID NO. 5) containing peptide (KNAGFELPLTGGSRI (SEQ ID NO. 9)) for 24 and 48 hrs to measure their respective hydrolysis activities. Representative HPLC traces are shown for the peptide control and each sortase mutant: peptide control (grey), CdSrtA$^{WT}$ (green), CdSrtA$^{2M}$ (blue), and CdSrtA$^{3M}$ (purple). Integration of the peak corresponding the full length LPLTG (SEQ ID NO. 5) peptide remaining after each incubation time reports on the amount of peptide processed by each construct. Those integrals were determined and activities were calculated relative to the extent of peptide processing by CdSrtA$^{WT}$ after 24 hours.

FIG. 12(A) Incubation of CdSrtA$^{3M}$ with 10 molar equivalents of pilin motif peptide and LPLTG (SEQ ID NO. 5) peptide does not result in ligation as determined by MALDI-MS, even after extended incubations. FIG. 12(B) Incubation of CdSrtA$^{3M}$ with equimolar amounts of $^{C}$SpaA and 10 molar equivalents of pilin motif peptide (DGWLQDVHVYPKHQALS (SEQ ID NO: 11)) also does not yield a detectable linkage by MALDI. FIG. 12(C) Incubation of equimolar $^{N}$SpaA and CdSrtA$^{3M}$ with a 10× molar excess of 'sort-tag' peptide (KNAGFELPLTGGSGRI (SEQ ID NO. 9)) results in robust and specific modification of Lys190 of $^{N}$SpaA, as shown by the characteristic mass shift in the MALDI spectra. For each spectra, the calculated mass of the theoretical transpeptidation linkage for each reaction is highlighted by a dashed red box.

FIG. 13(A) Representative traces are shown for each construct: peptide control (black), SaSrtA$^{WT}$ (green), SaSrtA$^{4M}$ (blue) and CdSrtA$^{3M}$ (red). The retention time of full length LPATG (SEQ ID NO. 5) peptide is outlined by a black box for clarity. FIG. 13(B) Quantification of hydrolysis activity was calculated by integrating under the peak of the full length peptide and subtracting that value from the integral obtained from the HPLC trace of LPATGpep (SEQ ID NO. 5) in isolation to determine the relative amount of peptide processed by each enzyme. The activity of each enzyme is plotted as the percentage of LPATGpep (SEQ ID NO. 5) hydrolyzed after 24 hours.

FIG. 14(A) Attaching peptides to proteins. FIG. 14(B) Joining proteins together. In both processes the linkage is established via a novel lysine isopeptide bond.

FIG. 16A shows gel data comparing transpeptidation activity of Cd-SrtA$^{3M}$ (left panel) and Cd-SrtA$^{\Delta}$ (right panel) variants. FIG. 16B shows graphed data comparing transpeptidation activity of Cd-SrtA$^{3M}$ and Cd-SrtA$^{\Delta}$ variants.

DETAILED DESCRIPTION OF THE INVENTION

Figure 1:
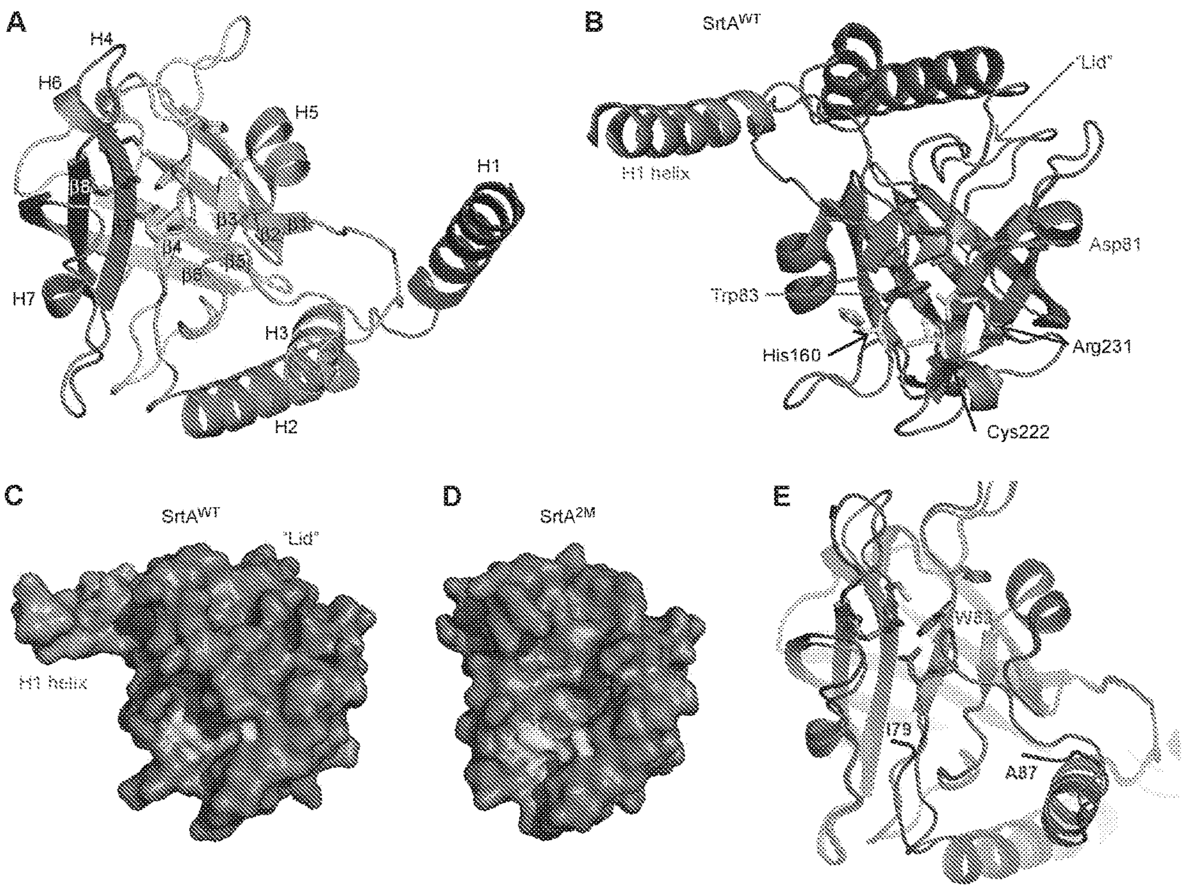
FIG. 1(C-D) Shown is hydrophobic surface rendering of wild-type SrtA ($SrtA^{WT}$) and the lid mutant ($SrtA^{2M}$) structures with the H1 helix and lid loop structures in red. The H1 helix of $SrtA^{2M}$ is absent and its lid structure is not visible, shown by a red dash line.

In the description of embodiments, reference may be made to the accompanying figures which form a part hereof, and in which is shown by way of illustration a specific embodiment in which the invention may be practiced. It is to be understood that other embodiments may be utilized and structural changes may be made without departing from the scope of the present invention. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Many of the aspects of the techniques and procedures described or referenced herein are well understood and commonly employed by those skilled in the art. The following provides a number of illustrative embodiments of the invention.

Aspects, Elements and Embodiments of the Invention

As disclosed herein, we have discovered that mutations in the lid region of Class C sortases provide these enzymes with a new activity, namely an ability to form isopeptide linkages between a threonine residue in a first polypeptide and a lysine residue in a second polypeptide. Illustrative working embodiments of the invention disclosed herein comprise a variant *Corynebacterium* diphtherias sortase (Cd-SrtA) having mutations in the lid region of the Cd-SrtA polypeptide, for example an active truncated variant of this enzyme (SEQ ID NO. 1) having at least two substitution mutations selected from the group consisting of D45G, W47G and N49A of SEQ ID NO:1 or at least 2 deletion mutations in amino acids 43-51 the polypeptide of SEQ ID NO: 1. In illustrative embodiments of the invention (see, e.g., the schematics shown in FIGS. 7, 9, 10 and 14), a protein of interest can expressed as a fusion protein such as with a $^{N}$SpaA polypeptide sequence comprising for example YKPN (SEQ ID NO. 6). In such embodiments, the protein of interest can then be conjugated to a detectable marker (or other agent) in the presence of a Cd-SrtA variant as disclosed herein by reacting the protein of interest with a peptide containing a LPLTG amino acid sequence coupled to the detectable marker (or other agent).

Illustrative Reagents and Reactions

We have discovered that the *Corynebacterium* diphtherias sortase (Cd-SrtA) enzyme can be precisely modified in a manner that allows it to be used as a new form of bioconjugation reagent. On the bacterial cell surface, Cd-SrtA functions as a transpeptidase that joins two proteins together. One protein contains a C-terminal LPLTG (SEQ ID NO. 5) amino acid sequence, and the other protein contains a pilin motif (WXXXVXVYPKH (SEQ ID NO: 12)) that harbors a reactive side-chain ε-amine lysine nucleophile (underlined) (FIG. 14*b*). Cd-SrtA catalyzes the formation of an isopeptide bond by cleaving the LPLTG sequence between the T and G residues, creating a thiol-acyl intermediate between the T residue and the catalytic cysteine 222 of Cd-SrtA. This intermediate is then resolved when a sidechain lysine nucleophile present in the pilin motif attacks the SrtA-acyl intermediate resulting in an isopeptide bond between the C-terminus of the T residue and the sidechain amine present on the lysine nucleophile. In the native reaction, LPLTG (SEQ ID NO: 5) sequence resides within the C-terminal tail of SpaA.

Atomic structures of Cd-SrtA have revealed that its active site is masked by a polypeptide appendage called a "lid". The lid inhibits the transpeptidation activity of the enzyme by preventing substrate binding. In the examples below we show that the strategic introduction of amino acid mutations into the lid activates the enzyme, enabling it to catalyze lysine isopeptide bond formation in vitro, whereas the wild-type Cd-SrtA protein is not active in vitro. At present, we have created two activated enzymes, Cd-SrtA$^{2M}$ (Cd-SrtA with D81G and W83G mutations) and Cd-SrtA$^{3M}$ (Cd-SrtA with D81G, W83G and N85A mutations). Cd-SrtA$^{3M}$ has the highest level of in vitro activity.

As disclosed herein, we show that Cd-SrtA$^{2M}$ can ligate its natural protein substrates via an isopeptide bond. Its substrates are two autonomously folded domains: $^{C}$SpaA containing the LPLTG sequence at its C-terminus (residues 491-495 of SpaA) and $^{N}$SpaA containing the pilin motif (residues 181-191 of SpaA). In work described below, we have extended these studies to demonstrate peptide labeling of proteins and protein-protein ligation.

As discussed in detail below, mutations in the lid region of Class C bacterial sortases can provide these enzymes with a new activity, namely an ability to form isopeptide linkages between a threonine residue in a first polypeptide and a lysine residue in a second polypeptide. The working embodiments of the invention disclosed herein utilize variants *Corynebacterium diphtheriae* sortase (Cd-SrtA) having deletion or substitution mutations in the lid region of a catalytic domain variant of a Cd-SrtA polypeptide (e.g. amino acids 43-51 of SEQ ID NO: 1). In this context, embodiments of the invention include compositions of matter comprising a variant polypeptide having at least 90% identity to *Corynebacterium diphtheriae* Class C sortase polypeptide of SEQ ID NO: 1 (or at least 90% identity to SEQ ID NO: 2, or at least 90% identity to SEQ ID NO. 41); wherein the *Corynebacterium diphtheriae* Class C sortase variant polypeptide comprises at least one amino acid substitution or deletion mutation in amino acids 43-51 of SEQ ID NO: 1; and the *Corynebacterium diphtheriae* Class C sortase variant polypeptide exhibits an increased ability to catalyze threonine-lysine isopeptide bond formation in vitro as compared to wild type *Corynebacterium diphtheriae* Class C sortase.

Typically in the compositions of the invention, the variant polypeptide comprises at least two substitution or deletion mutations in the lid region of the *Corynebacterium diphtheriae* Class C sortase, for example one or more substitution mutations selected from the group consisting of D45, W47 and N49 of SEQ ID NO: 1, and/or a plurality of deletion mutations in residues 43-51 of SEQ ID NO: 1. In certain embodiments of the invention, the variant polypeptide comprises substitution mutations D45G and W47G in SEQ ID NO: 1, and optionally the further substitution mutation N49A in SEQ ID NO: 1. Optionally, the *Corynebacterium diphtheriae* Class C sortase variant polypeptide in such compositions exhibits an ability to form isopeptide bonds in vitro that is at least 25% or 50% of the ability to form isopeptide bonds exhibited by a *Corynebacterium diphtheriae* sortase polypeptide comprising lid region substitution mutations D45G and W47G in the polypeptide of SEQ ID NO: 1 or one or more deletion mutations in ILDPWLNRA of SEQ ID NO: 1 (including all amino acids ILDPWLNRA), for example using an assay of isopeptide bond formation that is disclosed herein. In this context, the invention disclosed herein further provides methods of identifying class C sortase enzymes having a modified ability to form isopeptide bonds in vitro, namely by making systematic mutations in the amino acids of the lid region of such enzymes and then testing such mutants for an ability to form isopeptide using an assay of isopeptide bond formation that is disclosed herein.

Figure 16:
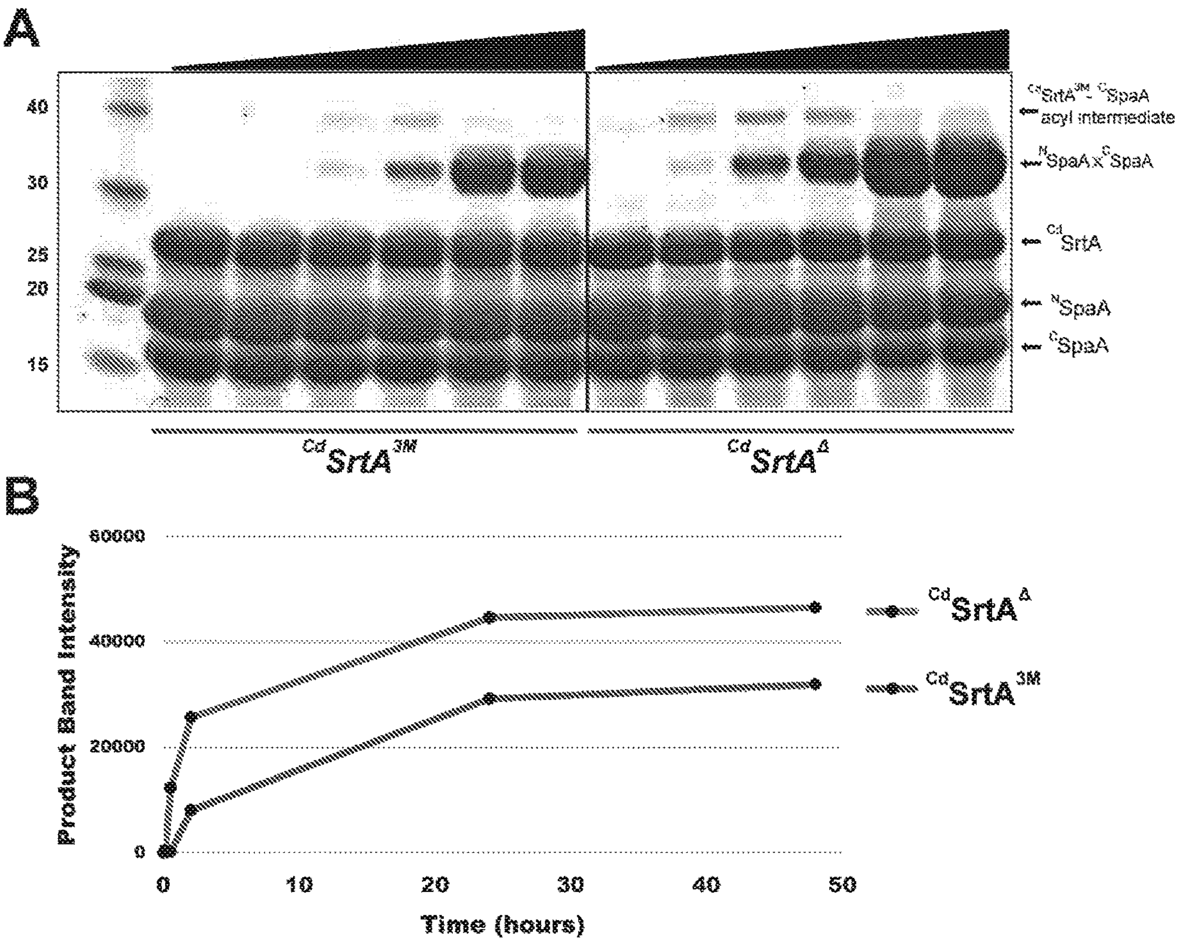
FIG. 16A-16B: Data showing transpeptidation activity of $^{Cd}$SrtA$^{\Delta}$ by gel-based assay.
Figure 17:
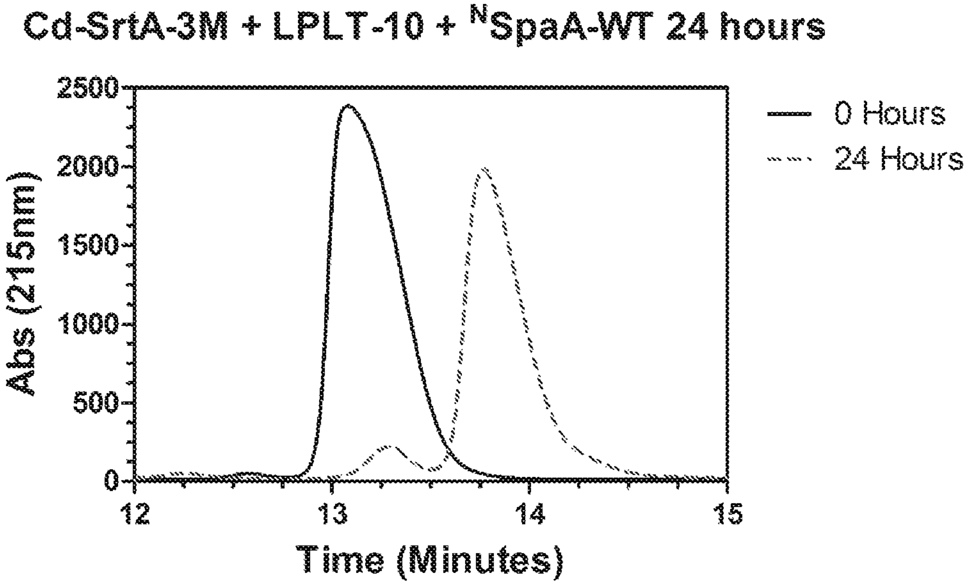
FIG. 17: Data showing transpeptidation activity of $^{Cd}$SrtA$^{\Delta}$ by gel-based assay. To more rigorously compare the Cd-SrtA$^{3M}$ and Cd-SrtA$^{\Delta}$ variants, we show graphed data from a quantitative HPLC assay in which sortase-catalyzed addition of a sorting signal peptide is tracked by reversed-phase high performance liquid chromatography. Importantly, this assay shows that the A construct has catalytic efficiency that is more than three-fold greater than the 3M construct (2.5 vs 0.7 $s^{-1}$/M). Results from a full kinetic characterization indicate that the $^{Cd}$SrtA$^{\Delta}$ sortase variant represents a marked kinetic improvement from previous variants (Table 2).

After discovering that iterative substitution mutations of the occlusionary "lid" structure of CdSrtA yielded incremental increases in transpeptidation product, we reasoned that removal of most or all residues comprising the lid structure would yield an even more active variant. Examination of the crystal structure of CdSrtA WT showed that the lid begins and ends at a similar position in the tertiary structure, providing evidence that complete deletion of the intervening residues would be tolerated and not preclude proper protein folding. Thus, we deleted nine residues from the lid ("ILDPWLNRA"), calling this new construct CdSrtA$^{\Delta}$. Expression of this engineered variant was robust and protein stability was comparable to other constructs. When we then assayed transpeptidation activity of CdSrtA$^{\Delta}$ by our gel-based assay (FIG. 16A). As evidenced by an accelerated accumulation of $^{N}$SpaA-$^{C}$SpaA crosslinked dimer product, CdSrtA$^{\Delta}$ proceeds with significantly enhanced kinetics as compared to the most catalytically efficient variant previously characterized, CdSrtA$^{3M}$ (FIG. 16B). To more rigorously compare the two variants, we developed a quantitative HPLC assay in which sortase-catalyzed addition of a sorting signal peptide is tracked by reversed-phase high performance liquid chromatography (FIG. 17). Importantly, this assay determined that the Δ construct has catalytic efficiency that is more than three-fold greater than the 3M construct (2.5 vs 0.7 s−1/M). Results from a full kinetic characterization indicate that the CdSrtA$^{\Delta}$ sortase variant represents a marked kinetic improvement from previous variants (Table 2).

Illustrative Applications

Creating Isopeptide-Linked Protein-Peptide Conjugates.

Creating isopeptide-linked protein-peptide conjugates is a promising use for the new technology disclosed herein as it enables peptide-based molecules to be attached to proteins via a robust isopeptide bond (see, e.g. the schematics shown in FIGS. 7, 9, 10 and 14). These molecules include peptide-based fluorophores, drugs, lipids, PET labels and sugars, among others. In such embodiments of the invention, a protein of interest can be expressed as a fusion protein with $^{N}$SpaA. The protein can then be labeled using Cd-SrtA by reacting it with a peptide containing a LPLTG amino acid sequence (SEQ ID NO. 5). Importantly, any molecule (drug, fluorophore etc.) that contains this peptide sequence can be used to label the protein.

Figure 15:
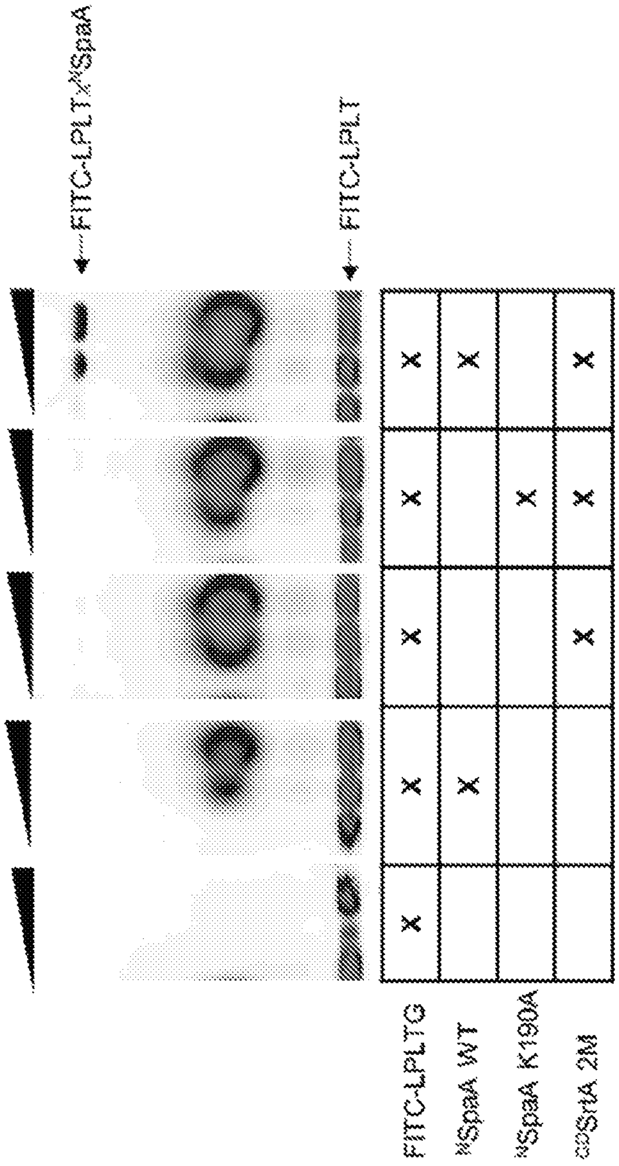
FIG. 15: Data showing protein-peptide ligation. Fluorescence imaging (excitation 488 nm, detection 515-545 nm) of SDS-PAGE gel with reactions containing listed components demonstrates the ability of Cd-SrtA$^{3M}$ to catalyze the addition of a fluorophore-labeled peptide specifically to K190 of $^{N}$SpaA. 3 timepoints for each reaction: 0, 24, 48h. The middle "splotch" is an artifact of the imaging process—not reaction product. Only the cross-linked species is produced.

We have also demonstrated Cd-SrtA$^{3M}$ catalyzed protein labeling with a peptide-fluorophore (see, e.g. FIG. 15). In this work the small ubiquitin-like modifier SUMO-protein was expressed as a fusion with the $^{N}$SpaA. The SUMO-$^{N}$SpaA was then reacted with a FITC-KNAGFELPLTG (SEQ ID NO: 13) peptide and Cd-SrtA$^{3M}$. We have obtained >90% modification of SUMO-$^{N}$SpaA.

Joining Proteins Together Via Lysine Isopeptide Bonds.

Embodiments of the invention can be used to join proteins together in vitro. In such embodiments, two fusion proteins are typically used. The first contains the protein of interest fused to $^{N}$SpaA (either at its N- or C-termini). The second protein is modified to contain a LPLTG motif (SEQ ID NO.

5) at the C terminus. The new reagent then ligates the proteins together, forming an isopeptide linkage between the threonine of the LPLTG (SEQ ID NO: 5) sequence (appended to the C-terminus of one protein) and the sidechain lysine residue of $^{N}$SpaA (fused to the other protein of interest).

Figure 6:
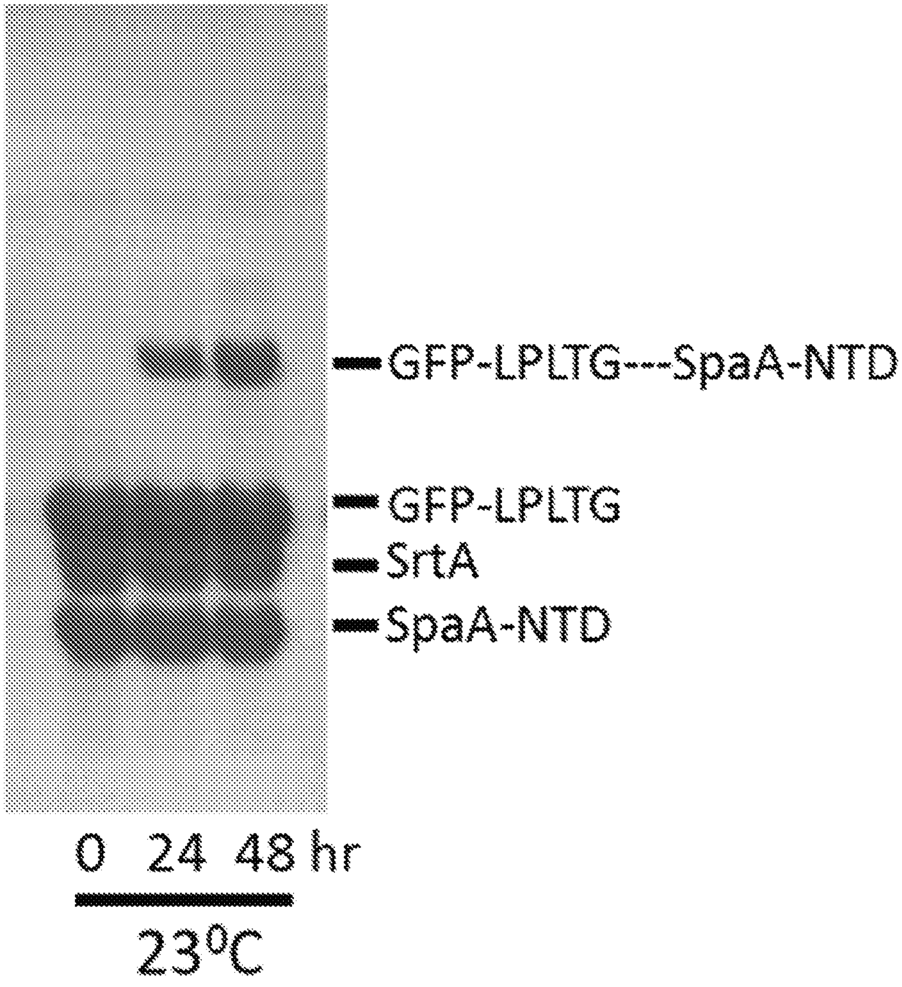
FIG. 6: Data showing protein-Protein ligation (GFP). SDS-PAGE results demonstrating isopeptide attachment of GFP-LPLTG (SEQ ID NO. 5) to $^{N}$SpaA. MALDI data support the isopeptide bond linkage.
Figure 7:
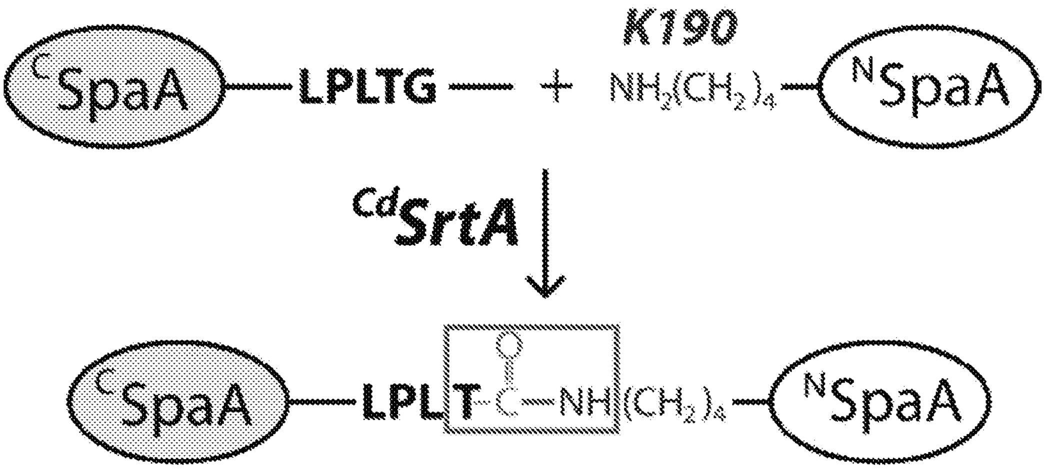
FIG. 7: Schematic showing CdSrtA-catalyzed isopeptide bond formation.

We have demonstrated protein-protein isopeptide coupling activity. As discussed in detail below, a GFP (green fluorescent protein) construct containing a C-terminal LPLTG (SEQ ID NO. 5) sequence was ligated to $^{N}$SpaA (FIG. 6). Ligation reactions containing 100 μM Cd-SrtA$^{2M}$ enzyme and 300 μM of substrates GFP-LPLTG (SEQ ID NO: 5) and $^{N}$SpaA were incubated at 23° C. and 4° C. in a standard reaction buffer (50 mM Tris-HCl pH 8.0, 300 mM NaCl). After 24 hours, GFP-LPLTG ligated to SpaA-NTD via an isopeptide bond is produced (FIG. 6). These studies also demonstrated that a SUMO-LPLTG (SEQ ID NO: 5) protein can be ligated to $^{N}$SpaA. We have further shown that the new enzyme reagent can be used to join GFP-LPLTG (SEQ ID NO: 5) to SpaB via an isopeptide bond. SpaB is an ancillary pilin in the same corynebacterial operon which contains a reactive lysine similar to $^{N}$SpaA, but it lacks the canonical WXXXVXVYPKH (SEQ ID NO: 12) pilin motif Typically, in these reactions we observe approximately 40% product formation in 48 hours. Isopeptide linkages have been confirmed by mass spectrometry.

In addition to the SpaA ligation systems reported above, the GFP-SpaB fusion has use in additional applications or fields. For example, the SpaB protein from *C. diphtherias* has inherent ability to tightly bind human pharyngeal cells. In this context, GFP-SpaB fusions can be used to label pharyngeal cells in vitro or in vivo. (i.e. labeling cells for bioassay, or labeling pharyngeal cells for medical procedures). Further, the system can be adapted to allow for small molecules (e.g. comprising a LPLTG (SEQ ID NO: 5) motif) to be coupled to SpaB, allowing for targeted small molecule payload delivery directly to pharyngeal cells. This can be useful for targeted delivery of therapeutics to pharyngeal infections, cancers, or other ailments which are presently difficult to treat.

The technology disclosed herein can be adapted for use with conventional applications that utilize Sa-SrtA. For example, embodiments of the invention can be used to generate antibody conjugates, nucleic acid-protein fusions, PEGylation/lipidated proteins, live cell-labeling, protein cyclization, silent labeling, domain labelling, to add proteins to solid supports and the like. A key difference between the invention disclosed herein and the conventional Sa-SrtA technology is that the new reagent unexpectedly creates isopeptide bonds, not peptide bonds. There are a number advantages to attaching proteins via isopeptide bonds including: (1) these linkages may be more resistant to proteolysis and therefore more stable, (2) the new enzyme reagent enables new sites on the protein to be labeled as Sa-SrtA is only efficient at modifying N- and C-six termini and (3) the new reagent can be used in combination Sa-SrtA enabling multiple molecules be to be attached to a single protein (e.g. ADCs that contain both an attached drug and a label for tracking tissue distribution).

Illustrative applications for the new reagents and methods disclosed herein include generating antibody-drug conjugates, generating nucleic acid-protein conjugates (e.g. conjugates useful to deliver the nucleic acid into the cell to modify the genome or modulate gene expression), covalent attachment of proteins and to solid supports and surfaces (e.g. to construct materials for biosensing and biocatalysis, lipid modification of proteins through sortase-catalyzed transpeptidation (e.g. to allow for the preparation of proteins that can be localized to regions of the cell via attached lipids (e.g. attachment of lipids to Ras and Rab proteins), the immobilization of proteins to biacore sensor chips and the like.

It has been reported that the *S. aureus* SrtA enzyme can form LPXTG ((SEQ ID NO: 5) where X is any amino acid) and lysine isopeptide conjugates (e.g. WO2015130846A2 and Bellucci J J, Bhattacharyya J, Chilkoti A. A non-canonical function of sortase enables site-specific conjugation of small molecules to lysine residues in proteins. Angewandte Chemie (International ed in English). 2015; 54(2):441-445. doi:10.1002/anie.201408126). This however is generally considered a side reaction, as the enzyme preferentially carries out a typical transpeptidation reaction with a primary amine N-terminal glycine nucleophile resulting in a normal peptide bond. Additionally, these studies only demonstrate ligation using canonical pilin motifs. To our knowledge this is the first report for utilization of an engineered sortase enzyme to robustly and specifically generate isopeptide protein bioconjugates with proteins containing a pilin motif (e.g. SpaA-NTD and SpaB). As well as the first reported SpaB bioconjugate. Moreover, the Cd-SrtA the only enzyme reagent available in the art that enables peptide and protein linkage via lysine isopeptide bonds at high yield.

EXAMPLES

The Examples below provide illustrative methods and materials that can be used in the practice the various embodiments of the invention disclosed herein.

EXAMPLE 1: IN VITRO RECONSTITUTION OF SORTASE-CATALYZED PILUS POLYMERIZATION REVEALS STRUCTURAL ELEMENTS INVOLVED IN PILIN CROSSLINKING

Part 1

Gram-positive sortase enzymes represent two broad functional categories—those that crosslink proteins to the cell wall, and those that can catalyze this reaction and polymerize proteins to build adhesive pilus fibers. In this Example, we disclose an in vitro reproduction of a robust pilus polymerization reaction using a variant of a corynebacterial pilus-specific sortase, in which the catalytic center is unmasked. By molecular modeling, we uncovered a conserved structural element of pilus-specific sortases critical for protein ligation in vitro and further demonstrated that the activated sortase ligates the isolated domains of the pilin harboring the donor and acceptor motifs for ligation. Besides enabling future molecular studies and antibiotic development, our system provides a powerful new platform for bioconjugation and protein engineering.

Adhesive protein polymers, called pili or fimbriae, are expressed on the cell envelope by many Gram-negative and Gram-positive bacteria, and they are critical for bacterial virulence (1). Many types of Gram-negative pili have been reported, including the well-studied retractable type IV, conjugative, and chaperone-assisted pili (2). These pili are formed by distinct pathways (2, 3); however, none of these pili are covalently linked polymers, unlike the sortase-catalyzed pili found in many Gram-positive bacteria, including *Actinomyces oris, Enterococcus faecalis, Bacillus cereus*, and numerous species of streptococci and lactobacilli (4-6).

One of the well-studied sortase-mediated pilus assembly systems involves *Corynebacterium diphtheriae* (7), the causative agent of pharyngeal diphtheria (8). *C. diphtheriae* produces three distinct pilus types (7, 9, 10), each comprised of a pilus tip adhesin, a pilus shaft made of the major pilin, and a base pilin that is covalently anchored to the cell wall (11). The archetypal SpaA-type pilus, which mediates adherence to the pharyngeal epithelium (12), consists of the tip pilin SpaC, shaft pilin SpaA, and pilus base SpaB (13). A pilus-specific sortase named SrtA is required for pilus polymerization (13), performing a repetitive, irreversible transpeptidation reaction that covalently links the pilin subunits via an isopeptide bond (14). Although each Spa pilin harbors a cell wall sorting signal (CWSS (SEQ ID NO. 19)), which starts with a conserved LPXTG (SEQ ID NO: 5) motif, followed by a stretch of hydrophobic amino acids and a positively charged tail (15), SpaA contains a pilin motif with the lysine residue K190 acting as a nucleophile for the aforementioned transpeptidation reaction (13). According to the current model (16), SrtA cleaves the LPXTG (SEQ ID NO: 5) motif of Spa pilins between threonine and glycine, forming acyl-enzyme intermediates between the threonine residue and the SrtA catalytic cysteine residue. This intermediate is then nucleophilically attacked by the reactive K190 of an incoming SpaA subunit. In pilus biogenesis, the SpaC-SrtA acyl enzyme intermediate forms first, resulting in the joining of the ε-amine group of K190 to the threonine carbonyl carbon atom in the LPXT (SEQ ID NO: 8) of SpaC. Pilus polymerization ensues when additional SpaA protomers are joined progressively to the pilus base by the SrtA enzyme via the same lysine-mediated transpeptidation reaction. Polymerization is terminated with the entry of SpaB to the pilus base (11), which is then anchored to the cell wall by the housekeeping sortase SrtF (17). This cell wall anchoring of pilus polymers is likely similar to that of surface proteins catalyzed by the prototype sortase A enzyme from *Staphylococcus aureus* (18, 19). While most of this biphasic model of pilus assembly in Gram-positive bacteria (6)—the pilus polymerization followed by cell wall anchoring—has experimentally been validated, the molecular determinants that make up a pilus-specific sortase and enables the enzyme to join proteins together remain unknown.

The SrtA enzyme is classified as a member of the class C sortase subgroup within the sortase superfamily that have the unique ability to cross-link proteins via lysine-threonine isopeptide bonds (20, 21). Although all sortases share a canonical β-barrel sortase superfamily fold (22, 23), class C enzymes are distinguished by the presence of a conserved N-terminal region that forms a "lid" that covers the active site structurally and functionally (24-26). In *Streptococcus pneumoniae*, X-ray crystallographic evidence originally suggested that the lid region was flexible, possibly modulating substrate binding; however, subsequent studies in solution utilizing NMR showed this region to be relatively rigid in the SrtC1 enzyme (24, 27-29). Mutations of the lid region in *A. oris* SrtC2 or *Streptococcus agalactiae* SrtC1 did not alter the pilus polymerizing activities in vivo (30, 31); nonetheless, the mutations caused enzyme instability and increased hydrolytic activity in *S. agalactiae* SrtC1 (30), supporting a regulatory role for the N-terminal lid. However, the unique structural properties that enable class C sortase enzymes to cross-link proteins remain unknown.

We report here the crystal structures of the *C. diphtherias* class C sortase SrtA lacking the signal peptide and transmembrane domain (referred to as $SrtA^{WT}$) and a mutant of this protein that has substitutions in the lid interface, which normally masks the catalytic pocket ($SrtA^{2M}$). Using these recombinant enzymes and a SpaA substrate that is missing the signal peptide and transmembrane domain, we succeeded in reconstituting the SpaA pilus shaft polymerization reaction in vitro, demonstrating that the removal of SrtA's lid not only unmasked the catalytic center structurally, but also enables the polymerizing activity in vitro. Subsequently, by structural modeling, phylogenic and mutational analyses, we identified two structural elements that enable SrtA to cross-link proteins. Importantly, we showed that the activated sortase can ligate the isolated pilin domains, thus defining the donor and acceptor motifs for the ligation reaction. The system we report provides a new platform for in vitro mechanistic investigations of Gram-positive pilus assembly, antibiotic development and biotechnological applications of protein modification and conjugation via a unique transpeptidation reaction.

Results and Discussions

Structure of the *C. diphtheriae* pillus-specific sortase—The archetypal SpaA pilus polymer produced by corynebacteria is built by the dedicated pilus-specific sortase named SrtA (7, 13). To gain insight into the mechanism of pilus polymerization, we determined the structure of SrtA by X-ray crystallography. We performed crystallization screens using a soluble fragment encompassing the catalytic domain of SrtA (residues 37-257, termed $SrtA^{WT}$), which was cloned, expressed, and purified from *E. coli*. $SrtA^{WT}$ crystallized as a homodimer in the $P6_1$ 2 2 space group. Diffraction data was collected to 2.1 Å resolution and phased by molecular replacement. The electron density for residues 37-248 was well defined enabling their structure to be modeled, while density for the remaining C-terminal residues is missing presumably due to a disordered state.

The overall structure of $SrtA^{WT}$ conforms to the typical sortase fold described previously (22), containing a 7-stranded β-barrel core flanked by several 310 and alpha helices (FIGS. 1A-1B). Three additional alpha helices are located at the N-terminus of $SrtA^{WT}$ (FIGS. 1A-1B), and contain the distinguishing 'lid' structure that occludes the enzyme's active site in a class C sortase (FIG. 1B). Interestingly, the H1-helix mediates homo-dimerization in the crystal structure, and is generally removed from the body of the enzyme (FIGS. 1A-1B), while helices H2 and H3 are positioned immediately adjacent to the active site, and are connected by a loop that contains the highly conserved DPW lid motif that interacts with the active site (FIG. 1A-B). Trp83 in the lid participates in aromatic stacking interactions with the active site Cys222 and nearby His160 residues. In addition, Asp81 within the motif interacts with the active site Arg231 residue, suggesting its regulatory role in lid positioning and pilin polymerization. Importantly, residues within the active site catalytic His-Cys-Arg catalytic triad are well resolved, and Cys222 can be modeled in two distinct positions with 50% occupancy both pointing towards and away from the active site (FIGS. 1A-1B).

To investigate the functional importance of the lid in polymerization, we next generated a recombinant SrtA mutant protein, in which the DPW lid motif (residues 81-83 of SEQ ID NO. 1) was mutated to GPG (SEQ ID NO: 14), hereafter described as $SrtA^{2M}$. We succeeded in determining the crystal structure of $SrtA^{2M}$ at 1.85-Å resolution using crystallization conditions that differed from those used for the WT protein (see Materials & Methods). In the electron density map for $SrtA^{2M}$, residues 80-86 that represent the lid were invisible. Presumably, the lid residue substitutions prevented contacts with the active site, causing the mutant lid to adopt a range of conformations. Remarkably, a second major difference between the two structures is the absence of interpretable electron density for the H1 helix in the SrtA$^{2M}$ lid-mutant, which might be caused by flexibility around the hinge between helices H1 and H2 and by the absence of stabilizing interactions with neighboring molecules in the crystals of SrtA$^{2M}$.

Figure 2:
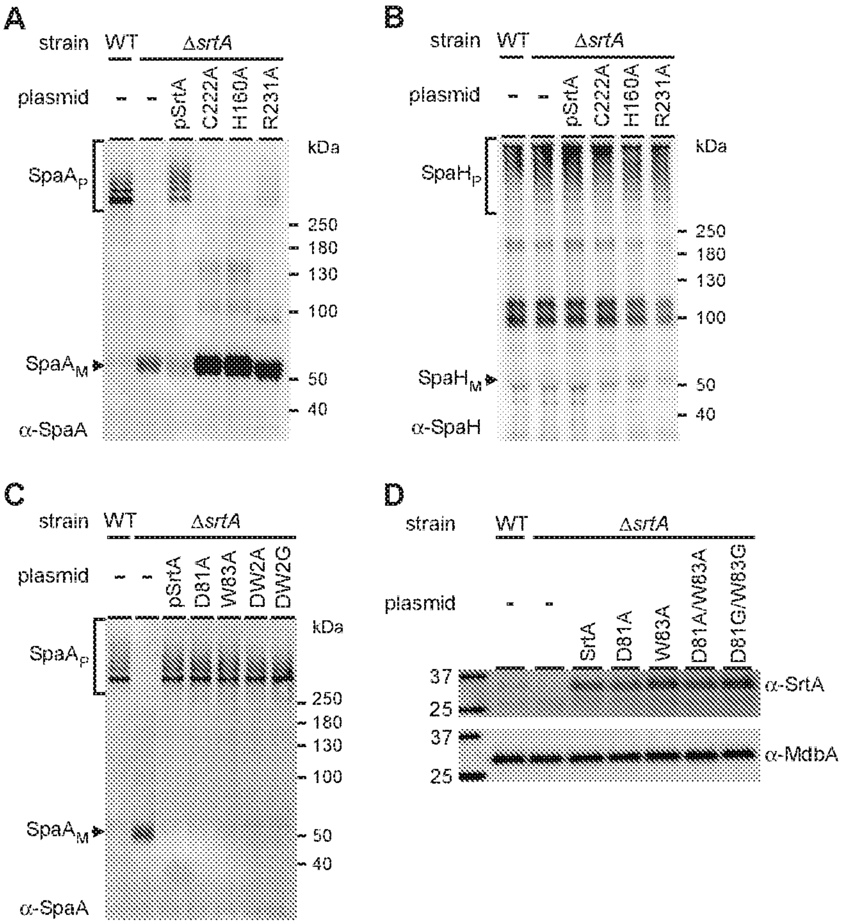
FIGS. 2A-2D: Catalytic residues are required pilus assembly in vivo—Cells of *C. diphtherias* strains in equivalent numbers were subjected to cell fractionation. Protein samples from cell wall fractions FIGS. 2(A-C) and protoplasts FIG. 2(D) were analyzed by immunoblotting with specific antibodies against SpaA (α-SpaA; A & C), SpaH (α-SpaH; B), and SrtA (α-SrtA; D), with α-MdbA as a membrane loading control. Pilus monomers (M), polymers (P), and molecular weight markers are indicated.

To evaluate the involvement of the predicted catalytic residues and the lid in pilus assembly, corynebacterial cells harboring WT and its isogenic mutants were subjected to cell fractionation, and protein samples were immunoblotted with specific antibodies against SpaA, the cognate substrate of SrtA that forms the pilus shaft (7, 13). As shown in FIG. 2A, SpaA polymers (P) were observed in cell wall fractions of the WT strain, but they were absent in the srtA deletion mutant, as previously reported (11). Ectopic expression of SrtA rescued the pilus assembly defect of the ΔsrtA mutant (FIG. 2A; third lane), and alanine-substitution of the catalytic residues C222, H160, and 8231 abrogated pilus assembly (FIG. 2A; last three lanes). In control experiments, we demonstrated that none of these mutations affected the assembly of the SpaH-type pili as expected (FIG. 2B) (9). Strikingly, the lid mutants are catalytically active in pilus polymerization. Compared to the wild-type and the complementing strains, strains expressing mutations in the DPW motif (residues 81-83 of SEQ ID NO. 1) still produced pilus polymers (FIG. 2C), and immunoblotting analysis of the membrane fractions revealed no changes in the SrtA protein level when the lid is mutated (FIG. 2D).

Thus, the overall structure of the *C. diphtheriae* SrtA' enzyme resembles class C sortases, or pilus-specific sortases, which possess a distinguishing feature of this class of enzymes, i.e. the lid region (16, 21). In agreement with previous studies (30, 31), the elimination of the lid's interaction at the catalytic pocket does not dramatically affect pilus polymerization in vivo.

In vitro reconstitution of archetypal *C. diphtheriae* SpaA pilus polymerization—Previous structural and biochemical studies of pilus-specific sortase enzymes in several streptococcal species implicate that the lid may modulate substrate entry into the active site (24, 25, 28, 30). We envisioned that a loss of lid closure might increase the accessibility of the active site. To test this hypothesis, we used the thiol-reactive reagent 4,4'-dithiodipyridine (DTDP) (32, 33), a to probe the solvent accessibility of the catalytic cysteine residue (C222). Disulfide exchange between thiol side chains of Cys resides and DTDP gives rise to 4-thiopyridone, which shows strong absorption at 324 nm (33). Recombinant proteins SrtA$^{WT}$ or SrtA$^{2M}$ (0.6 mg/ml) were rapidly mixed with 0.32 mM DTDP, and the rate of reaction between DTDP and C222 was monitored as an increase in absorbance at 324 nm. Time-dependent changes in absorbance were fit to single or double exponential equations to derive rates as described in the Materials and Methods. As shown in FIG. 3A, data for the wild-type enzyme SrtA$^{WT}$ best fit an equation with a single exponential rate of 2.17±0.02 min-1. In contrast, data for the lid anchor mutant best fit an equation with two much faster exponential rates of 228±7 min-1 and 16±3 min-1, (see inset to FIG. 3A), which indicates that the catalytic C222 was readily accessible in this mutant. The two rates may be due to slow exchange between two conformations in the mutant protein. If so, the conformation with the fastest rate is the dominant form since it represents 80% of the total change in absorbance.

The increased DTDP reactivity of the active site cysteine residue in SrtA$^{2M}$ described above raises the possibility that the mutant enzyme may be able to assemble pili in vitro—which has been difficult to reconstitute so far for pilus assembling sortases. We, therefore, sought to reconstitute pilus polymerization in vitro using various recombinant sortase enzymes and a soluble form of SpaA (residues 30-500), which is devoid of the N-terminal signal peptide and C-terminal membrane anchor domain (see a diagram in FIG. 3E). Sortases were mixed with SpaA at a 1:3 molar ratio, and at time 0, 24, and 48 h, aliquots were removed for SDS-PAGE analysis and Coomassie staining. In the SrtA$^{WT}$ samples, a few new high molecular weight (HMW) bands were weakly observed after 24 and 48 h of incubation, one migrating between 50 and 100 kDa markers and the others around 100 kDa (FIG. 3B, lanes SrtA$^{WT}$). Remarkably, with the SrtA$^{2M}$ enzyme, HMW SpaA polymers (SpaAP) were abundantly formed within 24 h and further increased after 48 and 72 h (FIG. 3B, lanes SrtA2M). Consistent with the results in FIG. 2A, the catalytically inactive enzyme with C222 replaced by alanine, SrtA$^{C222A}$, failed to produce any SpaA polymers (FIG. 3B, lanes SrtA$^{C222A}$). Intriguingly, removal of the H1 helix in the SrtA$^{2M}$ enzyme also abrogated pilus polymerization (FIG. 3B, lanes ΔSrtA$^{2M}$). The significance of this helix in the transpeptidation activity of sortase will be discussed below.

To visualize BMW SpaA polymers formed by SrtA$^{2M}$, the reaction mixtures after 72 h of incubation were subjected to electron microscopy, whereby aliquots were applied to nickel grids; bound proteins were washed and stained with 0.75% uranyl formate prior to viewing with an electron microscope. As shown in FIG. 3C, strands of SpaA polymers were observed in the reaction with the SrtA$^{2M}$ enzyme, not with a SpaA$^{K190A}$ mutant substrate defective in the nucleophilic attack, reporting for the first time the visualization of Gram-positive pilus polymers synthesized in vitro. The synthesized pilus polymers had the width of ~10 nm and the length ranging from ~200 to 500 nm, equivalent to 25 to 62 subunits, with each protomer measuring about 8 nm (34).

To determine if the recombinant SrtA$^{2M}$ enzyme faithfully catalyzes the pilus transpeptidation reaction, we determined whether the SpaA subunits in the BMW SpaA polymers were linked together via covalent lysine isopeptide bonds, in which the threonine residue of the LPLT (SEQ ID NO. 7) sorting signal was joined to the lysine residue within the pilin motif (13). Indeed, mass spectrometry (MS) analysis of excised HMW SpaA polymer SDS-PAGE bands revealed the presence of an isopeptide bond between the carbonyl carbon of T494 and the sidechain amine of Lys190 (FIG. 3D), as was observed in the native SpaA pili assembled in vivo (35). In line with the role of Lys190 in pilus polymerization, the SpaA mutant substrate with K190 replaced by alanine was unable to form polymers with the active SrtA$^{2M}$ enzyme (FIG. 3B, lanes SpaAK190A). Remarkably, the MS data revealed the presence of SrtA$^{2M}$ and SpaA in the marked band migrating between the 50 and 100 kDa markers in both SrtA$^{WT}$ and SrtA$^{2M}$ samples (FIG. 3B, asterisks), suggesting that the enzyme is joined to the SpaA substrate via a labile thioacyl bond forming an acyl-enzyme heterodimer intermediate. To our astonishment, the MS analysis also revealed the presence of SrtA$^{2M}$ in the HMW SpaA polymer bands migrating at and above the 100-kDa marker (FIG. 3B, lanes SrtA$^{2M}$, bracket). The results are in agreement with our previous identification of the native acyl-enzyme intermediates formed between SrtA and SpaA polymers in vivo in *C. diphtherias* as demonstrated by immunoblotting (36).

Figure 5:
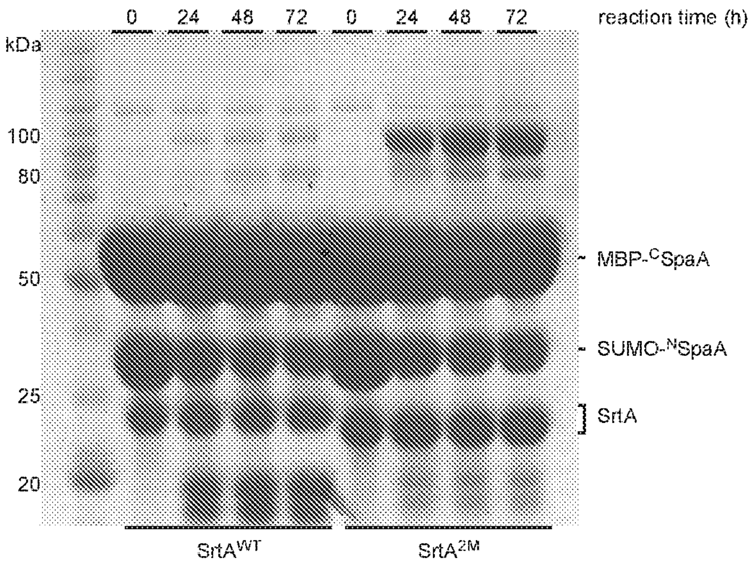
FIG. 5: SrtA containing the wild type lid is inactive in catalyzing crosslinking of the isolated domains. Fusion proteins between SUMO and the N-terminal SpaA domain ($^{N}$SpaA; residues 30 to 194) and between maltose-binding protein MBP and the C-terminal SpaA domain ($^{C}$SpaA; residues 350 to 500) were reacted with either the SrtA$^{WT}$ or SrtA$^{2M}$ enzyme at a 3:1 ratio, respectively. The reaction samples were analyzed by SDS-PAGE and Coomassie staining after 0, 24 h, 48 h, and 72 h of incubation.

To further probe the mechanism of SpaA pilus assembly, we dissected the SpaA molecule into two components: the N-terminal domain of SpaA-$^{N}$SpaA, residues 30-194—encompassing the pilin motif with the K190 nucleophile and the C-terminal domain—$^{C}$SpaA, residues 350-500—containing the CWSS (SEQ ID NO. 19) with the LPLTG (SEQ ID NO. 5) motif (FIG. 3E). The recombinant proteins were expressed in *E. coli* and purified. When the two isolated domains were mixed at equal concentration (300 μM) in a reaction with the lid substituted SrtA$^{2M}$ enzyme (100 μM), a dipolypeptide conjugate was readily formed (FIG. 3E). Significantly, the presence of the expected threonine-lysine isopeptide in this conjugate was confirmed by mass spectrometry. Furthermore, control reactions demonstrated that SrtA containing the wild type lid is considerably inactive in catalyzing crosslinking of the isolated domains (FIG. 5). Together, our results support the concept that the lid in class C sortase functions in molecular gating of substrate entry to the enzyme active site. This is first time that pilus polymerization in the Gram positive actinobacteria has been demonstrated in an in vitro reaction.

Structural elements in a sortase required for protein polymerization—To gain insight into how SrtA joins the SpaA proteins together during polymerization, we performed molecular modeling of the $^{N}$SpaA-SrtA-$^{C}$SpaA ternary complex, in which the isopeptide bond is modeled using our previously determined crystal structures of SpaA (PDB: 3HR6) (35) and the isolated SrtA (PDB:5K9A) proteins. We first generated a model of the SrtA-SpaA acyl-intermediate, juxtaposing the C-terminus of the C-terminal SpaA domain with the active site Cys222 residue in SrtA. Because the crystal structure of SpaA lacks the CWSS (SEQ ID NO. 19) that forms the acyl-intermediate with SrtA, we modeled the acyl-intermediate by placing the C-terminal domain of SpaA ~25 Å away from the active site cysteine to accommodate the 9 missing C-terminal residues that contain the CWSS (SEQ ID NO. 19). To construct the ternary complex we then positioned the coordinates of the SpaA N-terminal domain near the acyl intermediate to juxtapose the reactive lysine Lys190 of the pilin motif with the active site Cys222 residue (FIG. 4A). The resulting model of the ternary complex makes it readily obvious that the β7/β8 loop near the active site cysteine residue, as well as the N-terminal H1 helix in SrtA, are in contact with the SpaA N-terminal domain, raising the possibility that these elements might play a role in recognizing the region of SpaA that houses the reactive lysine nucleophile. Strikingly, a primary sequence alignment of SrtA and other class-C sortases indicates that they all contain a conserved TP(Y/L)XIN(S/T)H motif (SEQ ID NO. 10) within the β7/β8 loop (Table 1). This motif is clearly absent in other types of sortases that are known to attach proteins to the cell wall (class A, B, D and E enzymes) but unable to polymerize proteins. We thus postulated that the β7/β8 loop may play a role in conferring the polymerization activity in the class C enzymes.

In our model of the ternary reaction intermediate, the side chains of Y225, N228 and 5229 within the TP(Y/L)XIN(S/T)H motif (SEQ ID NO. 10) extend from the enzyme's surface in a position to contact $^{N}$SpaA. To explore their possible roles in catalysis, we constructed a series of mutants of the lid-opened SrtA$^{2M}$ mutant enzyme, in which each of these residues were individually replaced by alanine. The purified S229A and N228A mutant SrtA$^{2M}$ proteins were each defective in transpeptidation in vitro, as no isopeptide linked SpaA-SpaA product was produced even after 48 hours; the Y225A mutant protein had impaired transpeptidation activity as well, but to a lesser extent than the S229A and N228A mutants (FIG. 4C). Recall that the removal of the H1 helix in the SrtA$^{2M}$ enzyme also abrogates pilus polymerization (FIG. 3B, lanes ΔSrtA2M). We have determined that the absence of the H1 helix does not significantly affect the structure of the enzyme since the 1H-15N HSQC spectra of SrtA$^{2M}$ and ΔSrtA$^{2M}$ are similar. We conclude that specific residues within the β7/β8 loop and the presence of the H1 helix form a functionally important contact surface with $^{N}$SpaA. This is supported by experiments with a SrtA$^{2M}$ mutant harboring N165A substitution in the proximal β4/β5 loop, which showed that this mutant retained near wild-type activity (FIG. 4C; lanes SrtA$^{N165A}$).

The model of the ternary complex raises the possibility that critical residues in the β7/β8 loop and the helix H1 may only be required for nucleophile recognition during the transpeptidation reaction, but not for the other step of catalysis in which the LPXTG (SEQ ID NO. 5) sorting motif is cleaved to form the thioacyl enzyme-substrate intermediate (4, 37). To test this hypothesis, we determined the importance of these structural elements in thioacyl intermediate formation, using an established HPLC-based assay (38, 39) and a SpaA derived peptide KNAGFELPLTGGSGRI (SEQ ID NO. 9) (SpaApep) as the substrate. The enzymes and SpaApep substrate were mixed at 1:10 molar ratio, and the loss of the intact peptide was monitored by HPLC with the hydrolysis activity of SrtA$^{2M}$ set as 100%. Consistent with a selective role in nucleophile recognition, none of the mutants exhibited any significant defect in cleaving the LPXTG (SEQ ID NO. 5) motif (FIG. 4D). Importantly, the wild-enzyme SrtA$^{WT}$ and ΔSrtA$^{2M}$ enzymes, each of which are inactive in the pilus polymerization assay (see FIG. 3B), cleaves the SpaApep substrate with an efficiency comparable to the activated SrtA$^{2M}$ mutant enzyme (FIG. 4D). Under these conditions, the hydrolysis kinetics of the SrtA$^{WT}$, SrtA$^{2M}$, and ΔSrtA$^{2M}$ enzymes displayed comparable Vmax of 5.5±0.5, 6.3±1.1, and 6.3±0.7 μM/h, respectively. These results prompt us to propose that the conserved TP(Y/L)XIN(S/T)H (SEQ ID NO. 10) motif within the β7/β8 loop is a hallmark feature of the class C sortases that enable molecular recognition of the pilin motif lysine nucleophile in their cognate substrates. The H1 helix appears to play a similar role; however, it is not well conserved in class C sortases.

Figure 3:
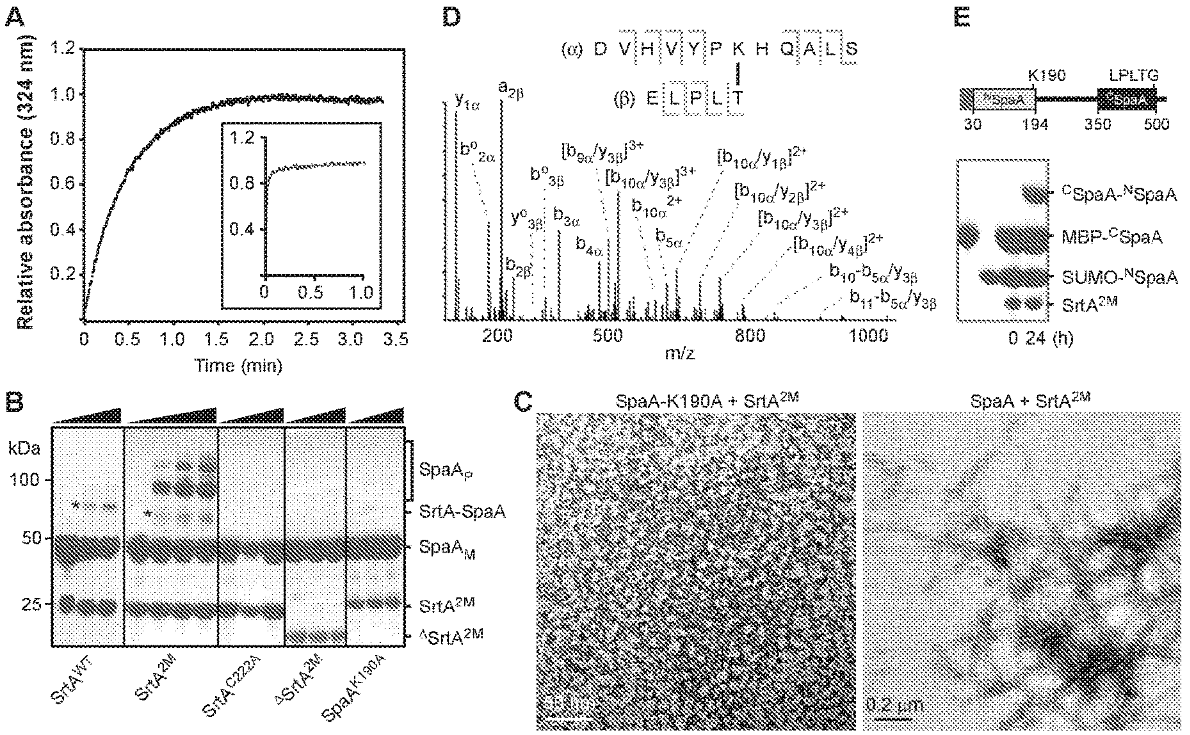
FIGS. 3A-3E. Involvement of the lid in pilus polymerization in vitro—FIG. 3(A) Accessibility of the thiol group of the active site C222 residue in $SrtA^{WT}$ (main panel) or $SrtA^{2M}$ (insert) enzymes was determined by stopped-flow experiments, whereby the reaction between the thiol-reactive reagent, 4, 4'-dithiodipyridine (DTDP), and C222 was monitored by absorbance at 324 nm. The experiments were performed in triplicate.
Figure 4:
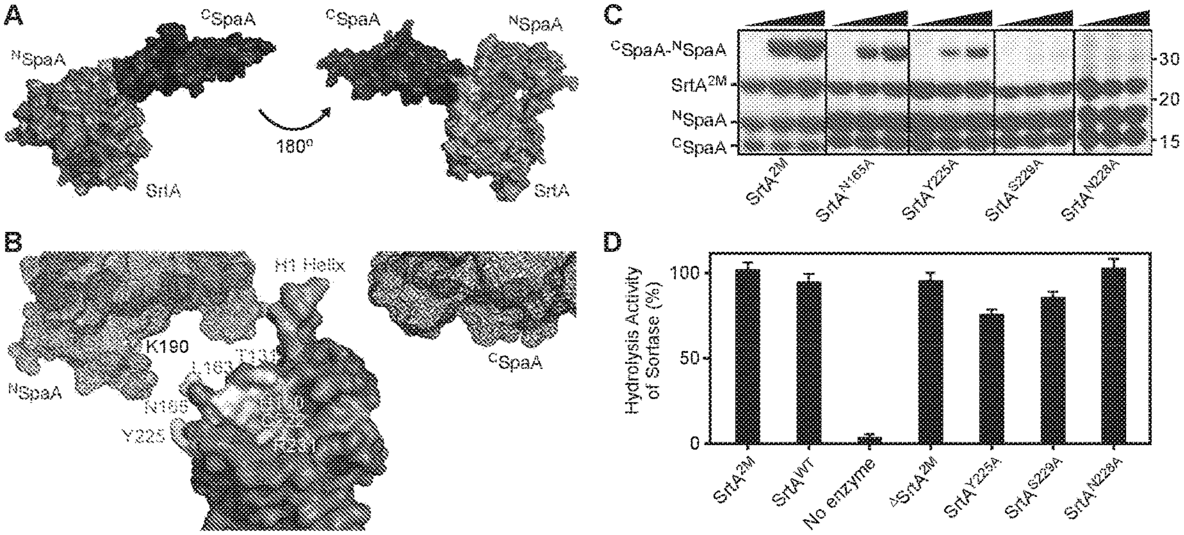
FIGS. 4A-4D. Structural modeling reveals SrtA residues critical for transpeptidation activities.

In conclusion, we reported here the high-resolution crystal structures of the *C. diphtherias* pilus-specific sortase SrtA enzyme (SrtA$^{WT}$) and a mutant form of the enzyme with mutations in the lid region (SrtA$^{2M}$) and through these, illuminated some of the basic features of the sortase that functions to polymerize pilus proteins in Gram-positive bacteria. The structure of the wild-type enzyme displayed a characteristic "closed" configuration of a class C sortase with its catalytic site occluded by a molecular lid (FIG. 1). By introducing specific amino acid substitutions within the lid, we were able to generate an enzyme whose catalytic pocket displayed an open conformation with no other major perturbations detected in the atomic structure. The functional importance of these two states of the enzyme was demonstrated by our ability to reconstitute a robust pilus polymerization reaction in vitro using the cognate shaft pilin. While the wild type form could not polymerize the shaft pilin in a reaction, the "opened"-lid version of the enzyme is highly active. We showed that the activated enzyme was able to recognize the sorting signal, form the relevant acyl-enzyme intermediate, recognize the pilin motif lysine residue and catalyze isopeptide bond formation conjugating lysine of one pilin protomer with threonine of another protomer (FIG. 3). We then utilized structural modeling to identify specific structural elements conserved in a pilus-specific sortase which are important for catalyzing the transpeptidation reaction in vitro (FIG. 4). Significantly, we showed that the separated domains of the pilin, one containing the pilin motif and the other containing the sorting motif could be ligated efficiently to produce a di-polypeptide conjugate containing the Lys-Thr isopeptide bond. This provides a novel and powerful protein ligation platform for engineering designer proteins that is mechanistically different from the "sortagging" technology developed with the archetypal sortase *S. aureus* which normally functions to crosslink surface proteins to the bacterial cell wall but do not polymerize proteins (40).

Materials and Methods

Bacterial Strains, Plasmids, and Media

*C. diphtherias* strains were grown in Heart Infusion (HI) broth (Becton Dickinson) or on HI agar plates at 37° C. When needed, kanamycin was added to the concentration of 25 μg ml-1. *E. coli* DH5a and BL21 (DE3), used for cloning and protein expression and purification, respectively, were grown either in Luria-Bertani (LB) or 2TY media at 37° C. in the presence of ampicillin (Amp) at 100 μg $ml^{-1}$.

In Vitro Reconstitution of Pilus Polymerization

In vitro reactions were carried out at room temperature and proteins were dissolved in assay buffer (50 mM Tris-HCl pH 8.0, 300 mM NaCl, 1 mM DTT). All reactions used a fixed 100 μM concertation of SrtA enzyme and 300 μM SpaA substrate (either full length, or each individual domain). Reactions were stirred gently by continuous rotation. Time points were taken at 0 h, 24 h, 48 h, and 72 h, and reactions were quenched by addition of two volumes of SDS-loading dye.

Probing Accessibility of the SrtA Active Site

Reaction rates of 4,4'-dithiodipyridine (DTDP) and SrtA proteins via the cysteine C222 residue were determined by stopped-flow experiments, which were performed at 23° C. using an Applied Photophysics Ltd. (Leatherhead, UK) Model SX.18 MV sequential stopped-flow spectrofluorimeter with a 150 watt Xe/Hg lamp, and a dead time of 1.7 ms. All triplicate reactions were carried out in Reaction Buffer (50 mM MOPS, 200 mM KCl, 1 mM EDTA, pH 7.5). Absorbance was monitored at 325 nm after rapidly mixing solutions in syringe A, which contained 0.6 mg/ml protein, and syringe B containing 0.32 mM DTDP. Reaction rates (k) were derived by fitting data to the following equations with 1 (equation 1) or two (equation 2) rates:

$$A=A\ \max{*}(1-e^{-kt}) \quad \text{equation 1}$$

$$A=A\ \max{*}(1-e^{-klt})+A\ \max\ 2{*}(1-e^{-k2t}) \quad \text{equation 2}$$

where A is absorbance at 324 nm at time, t, and Amax is the maximum absorbance.

Cell Fractionation and Western Blotting

Cell fractionation and Western blotting were followed according to published procedures with some modifications (41, 42). Briefly, mid-log phase cultures of *C. diphtherias* strains grown at 37° C. were normalized an OD600 of 1.0, and subject to cell wall protein extraction using mutanolysin (300 U/ml). Protein samples obtained from culture medium (S) and cell wall (W) were TCA precipitated and acetone washed. The protoplasts after the cell wall extraction were used for analysis of cell membrane-bound proteins. Protein samples were resuspended in SDS sample buffer containing 3% urea and heated at 100° C. for 10 min prior to SDS-PAGE analysis using 3-12% or 3-20% Tris-glycine gradient gels. Detection of proteins was performed by immunoblotting with specific antibodies (1:20,000 for α-SpaA; 1:4,000, α-SpaH; 1:5,000, α-MdbA, and 1:4,000, α-SrtA).

Mass Spectrometry of Pilus Polymers

Protein digestion and isopeptide bond identification were performed according to previous protocols (35, 43). Specifically, proteins entrapped in gel bands were reduced with 10 mM dithiothreitol (Sigma) at 60° C. for an hour and then alkylated with 50 mM iodoacetamide (Sigma) at 45° C. for a few minutes in the dark. These reduction and alkylation steps were skipped for the acyl intermediate samples. Samples were digested with 200 ng trypsin (Thermo Scientific) at 37° C. overnight. At the end of trypsin digestion, 200 ng of Asp-N endoproteinase (Thermo Scientific) were added for another overnight incubation.

Digested peptides were extracted from the gel bands in 50% acetonitrile/49.9% water/0.1% trifluoroacetic acid (TFA) and cleaned with C18 StageTip (44) before mass spectrometry analysis. Digested peptides were separated on EASY-Spray column (25 cm×75 μm ID, PepMap RSLC C18, 2 μm, Thermo Scientific) connected to an EASY-nLC 1000 nUPLC (Thermo Scientific) using a gradient of 5-35% acetonitrile in 0.1% formic acid and a flow rate of 300 nl/min for 30 minutes. Tandem mass spectra were acquired in a data-dependent manner with an Orbitrap Q Exactive mass spectrometer (Thermo Fisher Scientific) interfaced to a nanoelectrospray ionization source.

The raw MS/MS data were converted into MGF format by Thermo Proteome Discoverer 1.4 (Thermo Scientific). We wrote in-house programs to search for the isopeptides in two different approaches. The first approach was performed as previously described (35) and used calculated masses of predicted peptides containing the isopeptide linkage to guide the search. The second approach was based on the observation of published spectra as well as our own on the presence of ions specific for the fragments of ELPLT (m/z 215.138, 225.122, 243.132, 294.180, 312.190, 322.174 and 340.186). The in-house programs sifted through tens of thousands of mass spectra looking for this information specifically and pulled out mass spectra of interest for further analysis and manual validation.

Determination of SrtA Hydrolysis by an HPLC-Based Assay

In vitro hydrolysis reactions were performed based on the method developed by Kruger et al. (45). 50 μM SrtA (wild-type or mutant) was incubated with 500 μM KNAGFELPLTGGSGRI (SEQ ID NO. 9) (SpaApep) in 100 μl reactions at 37° C. for 48 h. The reactions were quenched by adding 50 μl of 1 M HCl and injected onto a Waters XSelect HSS C18 reversed phase HPLC column. Peptides were eluted by applying a gradient from 3 to 23% acetonitrile (in 0.1% trifluoroacetic acid) over 25 minutes at a flow rate of 1 ml/min. Elution of the peptides was monitored by absorbance at 215 nm. Peak fractions were collected and their identities were confirmed by MALDI-TOF mass spectrometry.

Electron Microscopy

For visualization of in vitro pilus polymers, 7 μl aliquots of pilus polymerization reactions diluted in half with water were applied onto nickel grids, washed 5 times with distilled water, and stained with 0.75% uranyl formate for 1 min prior to viewing by a JEOL JEM-1400 electron microscope.

EXAMPLE 1, PART 1 REFERENCES

1. Kline et al., (2010) *Trends Microbiol* 18(5):224-232.
2. Hospenthal et al., (2017) *Nat Rev Microbiol* 15(6):365-379.
3. Thanassi et al., (2012) *FEMS Microbiol Rev* 36(6):1046-1082.
4. Ton-That H & Schneewind O (2004) *Trends Microbiol* 12(5):228-234.
5. Telford et al., (2006) *Nat Rev Microbiol* 4(7):509-519.
6. Mandlik et al., (2008) *Trends Microbiol* 16(1):33-40.

7. Ton-That H & Schneewind O (2003) *Mot Microbiol* 50(4):1429-1438.
8. Rogers et al., (2011) *Adv Exp Med Biol* 715:91-103.
9. Swierczynski et al., (2006) *J Bacteriol* 188(17):6318-6325.
10. Gaspar A H & Ton-That H (2006) *J Bacteriol* 188(4): 1526-1533.
11. Mandlik et al., (2008) *Proc Natl Acad Sci USA* 105(37): 14147-14152.
12. Mandlik et al., (2007) *Mol Microbiol* 64(1):111-124.
13. Ton-That et al., (2004) *Mot Microbiol* 53(1):251-261.
14. Kang et al., (2007) *Science* 318(5856):1625-1628.
15. Navarre et al., (1999) *Microbiol Mol Biol Rev* 63(1): 174-229.
16. Siegel et al., (2016) *Curr Opin Microbiol* 34:31-37.
17. Swaminathan A, et al. (2007) *Mol Microbiol* 66(4):961-974.
18. Mazmanian et al., (1999) *Science* 285(5428):760-763.
19. Ton-That et al., (1999) *Proc Natl Acad Sci USA* 96(22): 12424-12429.
20. Dramsi et al., (2005) *Res Microbiol* 156(3):289-297.
21. Spirig et al., (2011) *Mol Microbiol* 82(5):1044-1059.
22. Jacobitz et al., (2017) *Adv Protein Chem Struct Blot* 109:223-264.
23. Khare et al., (2017) *Protein Sci* 26(8):1458-1473.
24. Manzano et al., (2009) *Biochemistry* 48(44):10549-10557.
25. Khare et al., (2011) *J Mot Blot* 414(4):563-577.
26. Persson K (2011) *Acta Crystallogr D Biol Crystallogr* 67(Pt 3):212-217.
27. Neiers F, et al. (2009) *J Mot Blot* 393(3):704-716.
28. Jacobitz A W, et al. (2016) *J Phys Chem B* 120(33): 8302-8312.
29. Manzano C, et al. (2008) *Structure* 16(12):1838-1848.
30. Cozzi R, et al. (2011) *FASEB* 25(6):1874-1886.
31. Wu C, et al. (2012) *J Bacteriol* 194(10):2531-2539.
32. Putkey J A, et al. (1997) *Biochemistry* 36(4):970-978.
33. Epps et al., (2002) *Chem Phys Lipids* 114(2):113-122.
34. Echelman D J, et al. (2016) *Proc Natl Acad Sci USA* 113(9):2490-2495.
35. Kang et al., (2009) *Proc Natl Acad Sci USA* 106(40): 16967-16971.
36. Guttilla I K, et al. (2009) *J Bacteriol* 191(18):5603-5612.
37. Ton-That et al., (2004) *Biochim Biophys Acta* 1694(1-3):269-278.
38. Aulabaugh A, et al. (2007) *Anal Biochem* 360(1):14-22.
39. Ton-That et al., (2000) *J Blot Chem* 275(13):9876-9881.
40. Antos J M, et al. (2017) *Curr Protoc Protein Sci* 89:15 13 11-15 13 19.
41. Chang et al., H (2011) *Mol Microbiol* 79(5):1236-1247.
42. Reardon-Robinson M E, et al. (2015) *Mol Microbiol* 98(6): 1037-1050.
43. Thevis et al., (2003) *J Proteome Res* 2(2):163-172.
44. Rappsilber et al., (2007) *Nat Protoc* 2(8):1896-1906.
45. Kruger et al., (2004) *Anal Biochem* 326(1):42-48.

Part 2

Recombinant Plasmids pSUMO-SrtA$^{WT}$ and its derivatives—To generate a recombinant plasmid expressing His tagged SrtA$^{WT}$ (residues 37 to 257), the srtA gene sequence without N-terminal signal peptide and C-terminal membrane spanning domains was PCR-amplified from the genomic DNA of *C. diphtherias* NCTC 13129 with appropriate primers and inserted into the pE-SUMO (LifeSensors) expression vector using the Gibson assembly method (New England BioLabs). pSUMO-SrtA$^{WT}$ was used as a template to generate D81A and W83A mutations (pSUMOSrtA$^{2M}$) as well as Y225A, S229A or N228A mutation, using site-directed mutagenesis carried out by QuickChange method (Agilent). Resulting plasmids were then transformed into XL10 for amplification prior to DNA sequence confirmation. Similarly, pSUMO ΔSrtA2M were generated using pSUMO-SrtA$^{2M}$ as a template, in which H1 helix (residues 37-54) was removed. The resulting plasmid was introduced into *E. coli* BL21 (DE3) after verification by DNA sequencing.

pMCSG-SrtA$^{WT}$ and its derivatives—For protein crystallization, the same srtA fragment as the above was cloned into the pMCSG7 expression vector by ligation-independent cloning (LIC) as previously reported (1). The resulting plasmid was introduced into *E. coli* DH5a for selection and DNA sequencing, and then *E. coli* BL21 (DE3). To generate pMCSG-SrtA$^{2M}$, pMCSG-SrtA$^{WT}$ was used as a template for inverse PCR amplification with a pair of phosphorylated primers carrying the intended mutation as previously described (1). The resulting linear PCR product was ligated before introduced into *E. coli* DH5a. The generated plasmid was verified by DNA sequencing prior to introduce into *E. coli* BL21 (DE3).

Recombinant SpaA plasmids—A plasmid expressing recombinant His-tagged SpaA protein of *C. diphtheriae* lacking the N-terminal signal peptide and C-terminal transmembrane domain (residues 30 to 500) was generated using the LIC method described above. The resulting plasmid (pMCSG-SpaA) was introduced into *E. coli* BL21 (DE3) after verification by DNA sequencing. Using the above site-directed mutagenesis method, pMCSG-SpaA was then used as a template to generate pMCSG-SpaA$^{K190A}$ that expresses the same SpaA molecule with lysine 190 replaced by alanine. To generate plasmids pSUMO-$^{N}$SpaA and pMBP-$^{C}$SpaA, which express the N-terminal (residues 30 to 194) and C-terminal (residues 350 to 500) domains of SpaA, pE-SUMO and pE-MAPLE were used, respectively, in the same cloning protocol as described for pSUMO-SrtA$^{WT}$ above. pSrtA and its derivatives—For srtA expression in *C. diphtheriae*, the *E. coli/Corynebacterium* shuttle vector pCGL0243 was used (2). pSrtA (3), a pCGL0243 derivative that expresses *C. diphtheriae* srtA under control of the spaA promoter, served as a template for site-directed mutagenesis, as described above, to generate various SrtA variants used in this study. The resulting plasmids were introduced into *E. coli* DH5a for DNA sequencing prior to electroporation into *C. diphtheriae* strains.

Protein Expression and Purification

For in vitro pilus polymerization, His-tagged proteins were purified according to a published procedure (4). Briefly, *E. coli* BL21 (DE3) cells harboring pSUMO-SrtA$^{WT}$, pSUMO-SrtA$^{2M}$, pMCSG-SpaA, pMCSG-SpaAK190A, pSUMO-$^{N}$SpaA, or pMBP-$^{C}$SpaA were grown in LB supplemented with ampicillin at 100 μg ml-1 at 37° C. until OD600 of ~0.6. Cells were equilibrated to 17° C. and treated with 1 mM IPTG before they were allowed to grow overnight at 17° C. to induce protein expression. Cells were then harvested by centrifugation (8,000 RPM for 20 min) and stored at −80° C. for further processing. SrtA and SpaA-derived proteins were purified His6x-SUMO-fusion using HisPure Co2+ IMAC resin (Thermo) per the manufacturer's instructions. Briefly, cell pellets were resuspended in 50 mM Tris-HCl pH 8.0, 300 mM NaCl, and 5 mM CaCl2 (lysis buffer) and lysed by sonication. Subsequent cell lysate was then fractionated by centrifugation (15,000 RPM for 1 hr) and the supernatant was loaded onto HisPure Co2+ IMAC resin. Proteins were then eluted from the resin using lysis buffer supplemented with 200 mM Imidazole. The His6x-SUMO tag was removed by the addition of His6x-

Ulp1 protease, and subsequent HisPure Co2+ purification. Protein purity was determined by SDS-PAGE analysis.

For crystallization, recombinant proteins were purified according to a published procedure (5). Briefly, *E. coli* BL21 (DE3) cells harboring pMCSG-SrtA' or pMCSG-SrtA$^{2M}$ was cultured in 2TY medium containing ampicillin at 100 μg ml-1 at 37° C. with shaking until OD600 of ~1.0. The culture was later induced with 0.4 mM IPTG and allowed to grow overnight at 18° C. with shaking. Cells were harvested and disrupted by sonication. The lysate containing SrtA was purified by using Ni-NTA (Qiagen) affinity chromatography with the addition of 5 mM β-mercaptoethanol in all buffers. The N-terminal His-tag and TEV restriction sequence of the protein was removed by the TEV protease (0.15 mg for 20 mg purified protein) incubated for 16 h at 4° C., and then passed through a Ni-NTA column to remove both the TEV protease and cleaved N-terminal tags. The final step of purification was gel-filtration on HiLoad 16/60 Superdex 200pg column (GE Healthcare) in crystallization buffer 10 mM HEPES buffer pH 7.5, 200 mM NaCl and 1 mM DTT. The protein was concentrated on Amicon Ultracel 10K centrifugal filters (Millipore) up to 24 mg/ml concentration.

Protein Crystallization, Data Collection, Structure Determination and Refinement The initial crystallization condition was determined with a sparse crystallization matrix at 4° C. and 16° C. temperatures using the sitting-drop vapor-diffusion technique as reported (5). The best crystallization condition for the SrtA$^{WT}$ protein was found in 0.1 M MES:NaOH buffer pH 6.5, 1.6 M ammonium sulfate and 10% dioxane at 4° C. The SrtA$^{2M}$ protein was crystallized in 0.2 M sodium chloride and 20% PEG 3350 at 4° C. The SrtA$^{WT}$ and SrtA$^{2M}$ protein crystals selected for data collection were soaked in the crystallization buffer supplemented with either 28% sucrose or 25% glycerol, respectively, and flash-cooled in liquid nitrogen. Single-wavelength X-ray diffraction data were collected at 100 K temperature at the 19-ID beamline using the program SBCcollect. The intensities were integrated and scaled with the HKL3000 suite (6). The SrtA structures were determined by molecular replacement using the HKL3000 suite incorporating following programs: MOLREP (7), SOLVE/RESOLVE (8), and ARP/wARP (9). The coordinates for the *A. oris* sortase SrtC-1 (10) (PDB:2XWG) were used as the starting model for the SrtAWT structure. Several rounds of manual adjustments of structure models using COOT (11) and refinements with Refmac program (12) from CCP4 suite (13) were performed. The stereochemistry of the structure was validated with PHENIX suite (6) incorporating MOLPROBITY (14) tools. Atomic coordinates and structure factors of SrtA$^{WT}$ and SrtA$^{2M}$ were deposited into the Protein Data Bank as 5K9A and 6BWE, respectively.

EXAMPLE 1, PART 2 REFERENCES

1. Reardon-Robinson M E, et al. (2015) A thiol-disulfide oxidoreductase of the Grampositive pathogen *Corynebacterium diphtherias* is essential for viability, pilus assembly, toxin production and virulence. *Mol Microbiol* 98(6): 1037-1050.
2. Chang C, Mandlik A, Das A, & Ton-That H (2011) Cell surface display of minor pilin adhesins in the form of a simple heterodimeric assembly in *Corynebacterium diphtherias. Mol Microbiol* 79(5): 1236-1247.
3. Guttilla I K, et al. (2009) Acyl enzyme intermediates in sortase-catalyzed pilus morphogenesis in gram-positive bacteria. *J Bacteriol* 191(18):5603-5612.
4. Bornhorst J A & Falke J J (2000) Purification of proteins using polyhistidine affinity tags. *Methods Enzymol* 326: 245-254.
5. Reardon-Robinson M E, et al. (2015) A Disulfide Bond-forming Machine Is Linked to the Sortase-mediated Pilus Assembly Pathway in the Gram-positive Bacterium *Actinomyces oris. J Biol Chem* 290(35):21393-21405.
6. Adams P D, et al. (2002) PHENIX: building new software for automated crystallographic structure determination. *Acta Crystallogr D Biol Crystallogr* 58(Pt 11): 1948-1954.
7. Vagin A & Teplyakov A (1997) MOLREP: an automated program for molecular replacement. *Journal of Applied Crystallography* 30:1022-1025.
8. Terwilliger T C (2003) SOLVE and RESOLVE: automated structure solution and density modification. *Methods Enzymol* 374:22-37.
9. Morris R J, Perrakis A, & Lamzin V S (2003) ARP/wARP and automatic interpretation of protein electron density maps. *Methods Enzymol* 374:229-244.
10. Persson K (2011) Structure of the sortase AcSrtC-1 from *Actinomyces oris. Acta Crystallogr D Biol Crystallogr* 67(Pt 3):212-217.
11. Emsley P & Cowtan K (2004) Coot: model-building tools for molecular graphics. *Acta Crystallogr D Biol Crystallogr* 60(Pt 12 Pt 1):2126-2132.
12. Murshudov G N, Vagin A A, & Dodson E J (1997) Refinement of macromolecular structures by the maximum-likelihood method. *Acta Crystallogr D Biol Crystallogr* 53(Pt 3):240-255.
13. Collaborative Computational Project N (1994) The CCP4 suite: programs for protein crystallography. *Acta Crystallogr D Biol Crystallogr* 50(Pt 5):760-763.
14. Davis I W, Murray L W, Richardson J S, & Richardson D C (2004) MOLPROBITY: structure validation and all-atom contact analysis for nucleic acids and their complexes. *Nucleic Acids Res* 32(Web Server issue): W615-619.
15. Ton-That H & Schneewind O (2003) Assembly of pili on the surface of *Corynebacterium diphtherias. Mol Microbiol* 50(4): 1429-1438.
16. Ankri S, Reyes O, & Leblon G (1996) Electrotransformation of highly DNA-restrictive corynebacteria with synthetic DNA. *Plasmid* 35(1):62-66.

EXAMPLE 2: SITE-SPECIFIC CHEMOENZYMATIC LABELLING OF LYSINE RESIDUES USING THE PILIN POLYMERIZING SORTASE FROM *CORYNEBACTERIUM DIPHTHERIAE*

Proteins that are site-specifically modified with peptides and chemicals have applications as therapeutics, imaging tools, diagnostic reagents and novel materials. Here we show that the sortase enzyme from *Corynebacterium diphtheriae* can be used to attach peptides to a protein via a specific lysine-isopeptide bond. Using rational mutagenesis we created CdSrtA$^{3M}$, an activated cysteine transpeptidase that catalyzes in vitro isopeptide bond formation. CdSrtA$^{3M}$ mediates bioconjugation to a specific lysine residue within a fused domain derived from the SpaA protein. Modifications yields greater than >95% can be achieved. We show that CdSrtA$^{3M}$ can be used with the *S. aureus* SrtA enzyme, enabling dual, orthogonal protein labeling via lysine isopeptide- and backbone peptide-bonds.

Methods that site-specifically functionalize proteins are of significant interest for applications including therapeutics, imaging tools, diagnostic reagents and novel materials. The first sortase to be developed into a protein engineering tool was from *Staphylococcus aureus* (SaSrtA)[1-4]. It catalyzes a transpeptidation reaction that covalently modifies the protein via a backbone peptide bond, by joining peptide segments that contain a LPXTG 'sort-tag' and an N-terminal oligoglycine amine group[5,6]. Several groups have now optimized the reaction to modify proteins with a range of molecules, including drugs, lipids, sugars, fluorophores, and peptides[7-14]. While SaSrtA is powerful tool for protein engineering, it is almost exclusively used to modify target proteins at their N- or C-termini. Although SaSrtA labeling of internal lysine side chains can occur, this process is a side reaction and has low sequence specificity[9,15,16] In this example we show that a mutationally activated sortase enzyme from *Corynebacterium diphtheriae* (CdSrtA) can be used to site-specifically attach peptides to a protein via a lysine-isopeptide bond. CdSrtA and SaSrtA have orthogonal activities, enabling dual peptide-fluorophore labeling of a protein via lysine isopeptide- and backbone peptide-bonds, respectively. Pathogenic Gram-positive bacteria use specialized sortase enzymes to construct pili. Pili are thin cross-linked fibers (0.2-3.0 μm×2-6 nm) that project from the cell surface to mediate bacterial adherence to host tissues, biofilm formation and host immunity modulation[17-19]. These structures are distinct from pili produced by Gram negative bacteria because their protein subunits (called pilins) are covalently linked to one another via lysine-isopeptide bonds, which confers enormous tensile strength.

Recently, we reconstituted in vitro the assembly which builds the archetypal SpaA-pilus in *C. diphtheriae*, the causative agent of pharyngeal diphtheria[20]. CdSrtA functions as a pilin polymerase, performing a repetitive transpeptidation reaction that covalently links adjacent SpaA pilin subunits together via lysine-isopeptide bonds. As shown in scheme 1 in FIG. 7, CdSrtA crosslinks adjacent SpaA proteins by connecting their N-($^{N}$SpaA, residues 30-194) and C-terminal ($^{C}$SpaA, residues 350-500) domains, which contain reactive WxxxVxVYPK (SEQ ID NO. 16) pilin motif and LPLTG (SEQ ID NO. 5) sorting signal sequences, respectively. In the reaction, CdSrtA first cleaves the LPLTG (SEQ ID NO. 5) sequence in $^{C}$SpaA between the threonine and glycine, forming acyl-enzyme intermediate in which catalytic C222 residue in CdSrtA is joined to $^{C}$SpaA's threonine carbonyl atom. This transient intermediate is then nucleophilically attacked by the reactive K190 within $^{N}$SpaA's pilin motif resulting in a T494-K190 isopeptide bond between $^{C}$SpaA and $^{N}$SpaA domains within adjacent pilin subunits. Previously, we demonstrated that wild-type CdSrtA is catalytically inactive in vitro because it contains an N-terminal polypeptide segment, called a lid, which masks the enzyme's active site and prevents sorting signal substrate access (FIG. 8A)[21-25]. Moreover, we showed that it was possible to activate the enzyme by introducing D81G and W83G lid mutations, creating CdSrtA2M (residues 37-257 of CdSrtA with D81G/W83G mutations) that is capable of site-specific ligation of the isolated $^{N}$SpaA and $^{C}$SpaA domains[20].

Figure 8:
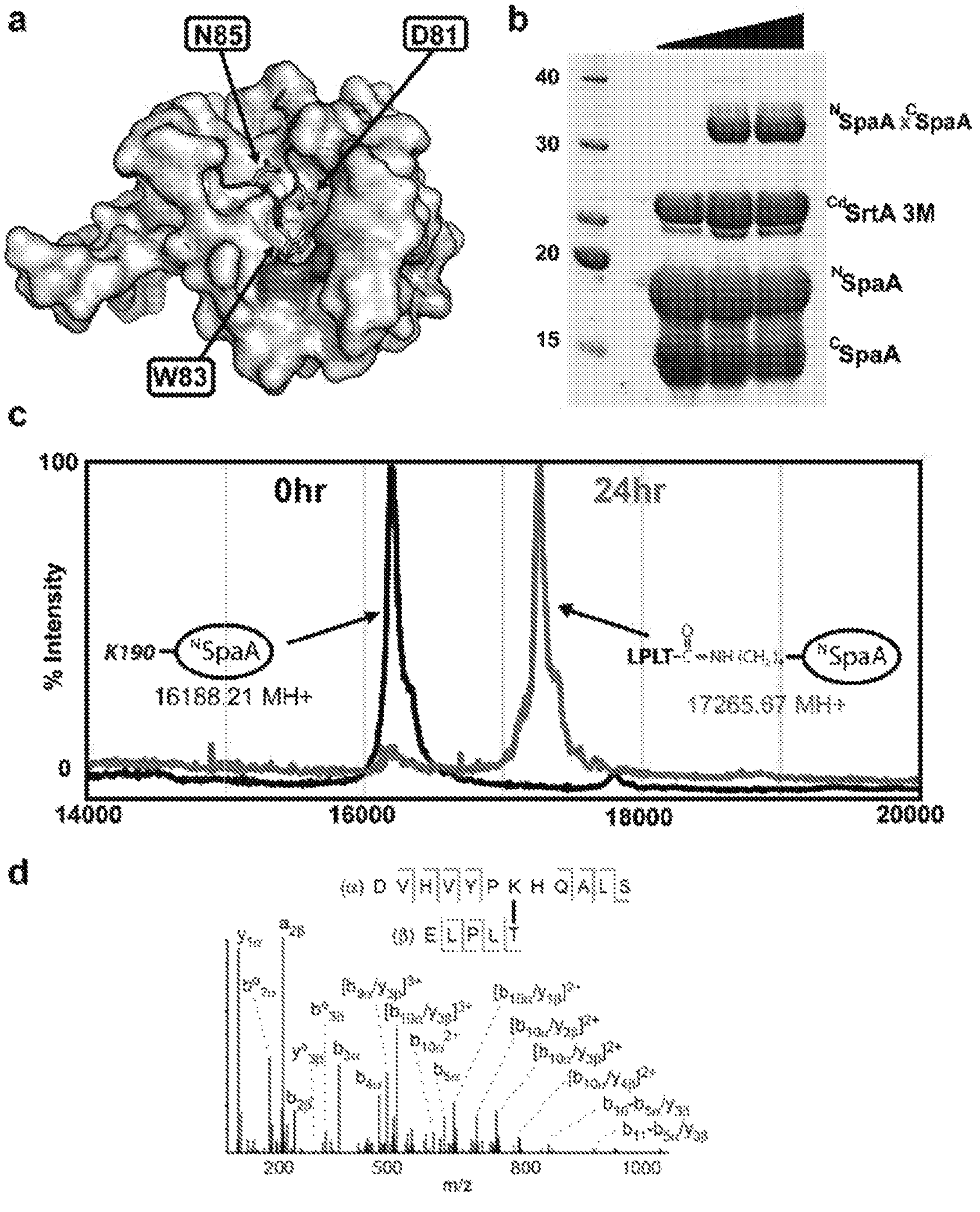
FIGS. 8A-8D. Mutationally activated CdSrtA catalyzes lysine-isopeptide bond formation.
Figure 9:
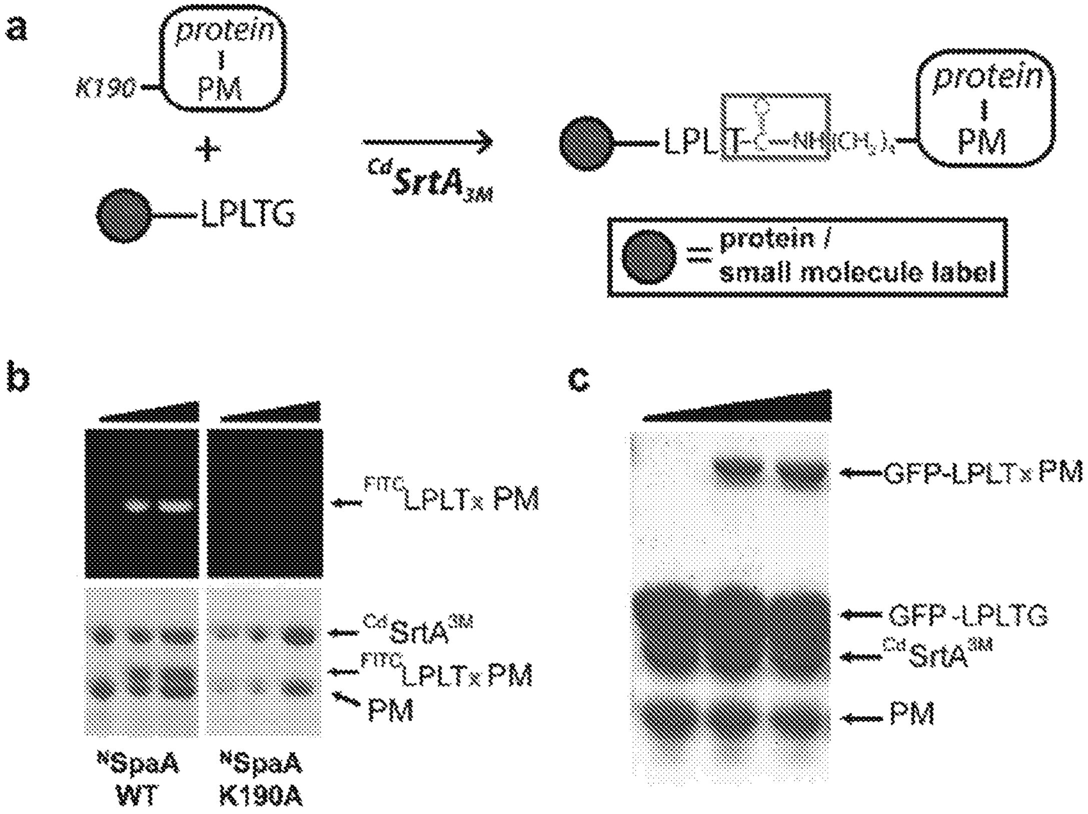
FIGS. 9A-9C. Labeling proteins via a lysine-isopeptide bond with CdSrtA$^{3M}$.
Figure 10:
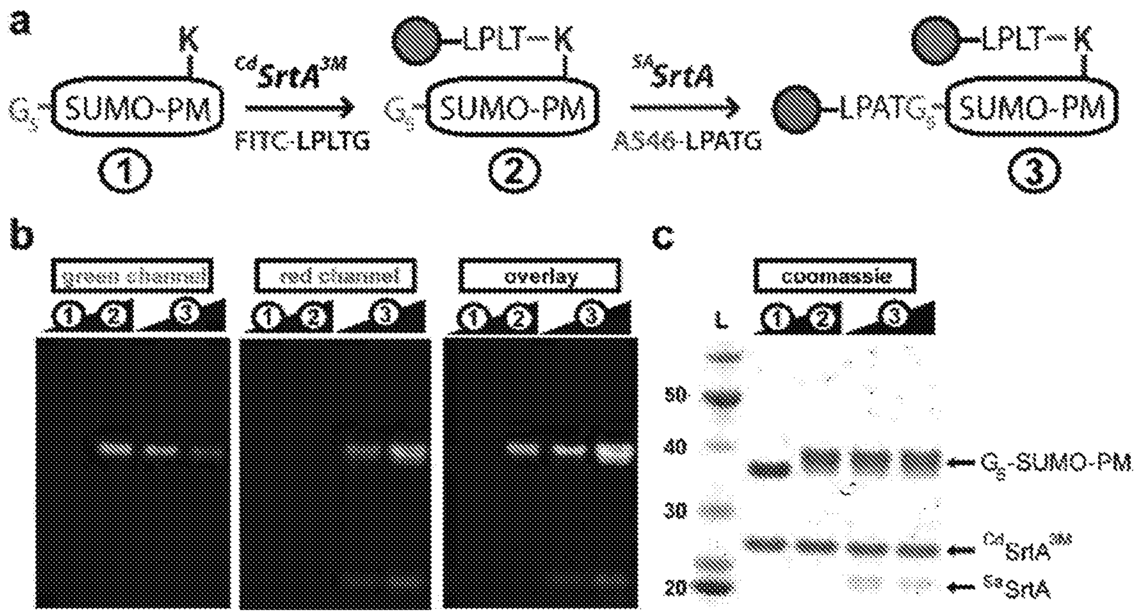
FIGS. 10A-10C. Orthogonal protein labeling with CdSrtA$^{3M}$ and SaSrtA.
Figure 11:
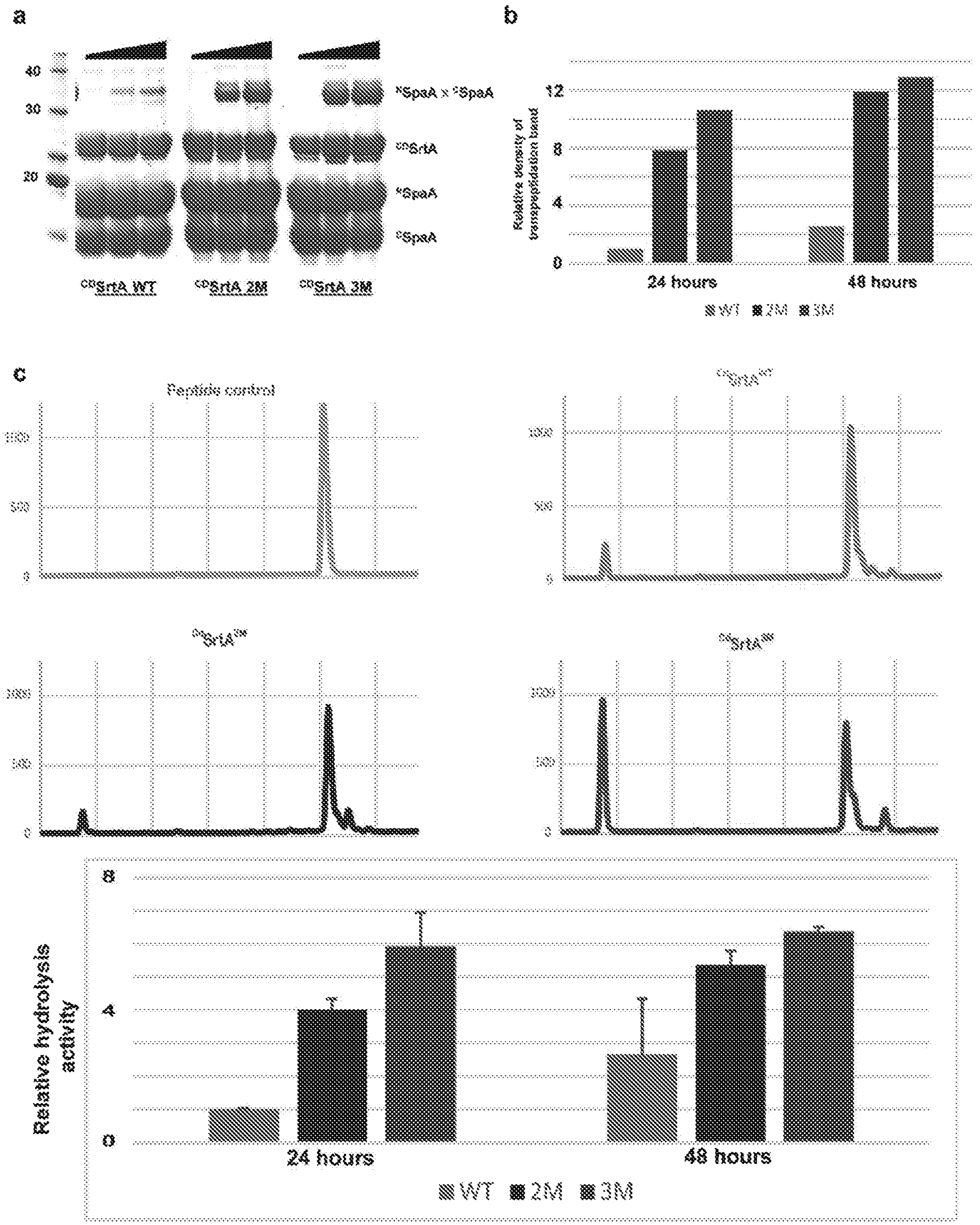
FIGS. 11A-11C: Relative activities of each CdSrtA mutants.

Toward the goal of creating a lysine modifying bioconjugation reagent we improved the ligation activity of CdSrtA$^{2M}$ by introducing additional mutations into its inhibitory lid structure and defined substrate determinants required for catalysis. In addition to the aforementioned D81 and W83 mutations in CdSrtA$^{2M}$, inspection of the crystal structure reveals three residues within the lid that may stabilize its positioning over the active site (179, N85, K89). The ligation activities of three triple mutants of CdSrtA containing the D81G and W83G alterations, as well I79R, N85A or K89A substitutions were determined. A D81G/W83G/N85A triple mutant, hereafter called CdSrtA$^{3M}$, has the highest level of ligation activity (FIGS. 8B and 11). After a 24 hour incubation with the isolated $^{N}$SpaA and $^{C}$SpaA domains, CdSrtA$^{3M}$ produces 10.6-fold more cross-linked $^{N}$SpaAx$^{C}$SpaA product than CdSrtA$^{WT}$ and 35% more product than CdSrtA$^{2M}$ (FIG. 11). The mutations in CdSrtA$^{3M}$ presumably further displace its lid, thereby facilitating enhanced binding of $^{C}$SpaA's LPLTG (SEQ ID NO. 5) sorting signal and subsequent acylation by C222. This is substantiated by our finding that the CdSrtA$^{3M}$ triple mutant exhibits the highest level of activity in a HPLC-based sorting signal cleavage assay that reports on formation of the acyl-enzyme intermediate (FIG. 11) and previous studies that have shown that alterations in the lid increase C222 reactivity with 4,4'-dithiodipyridine[20]. The $^{N}$SpaA and $^{C}$SpaA domains are joined by CdSrtA$^{3M}$ residues located within the pilin motif and LPXTG (SEQ ID NO. 5) sorting signal elements.

Figure 12:
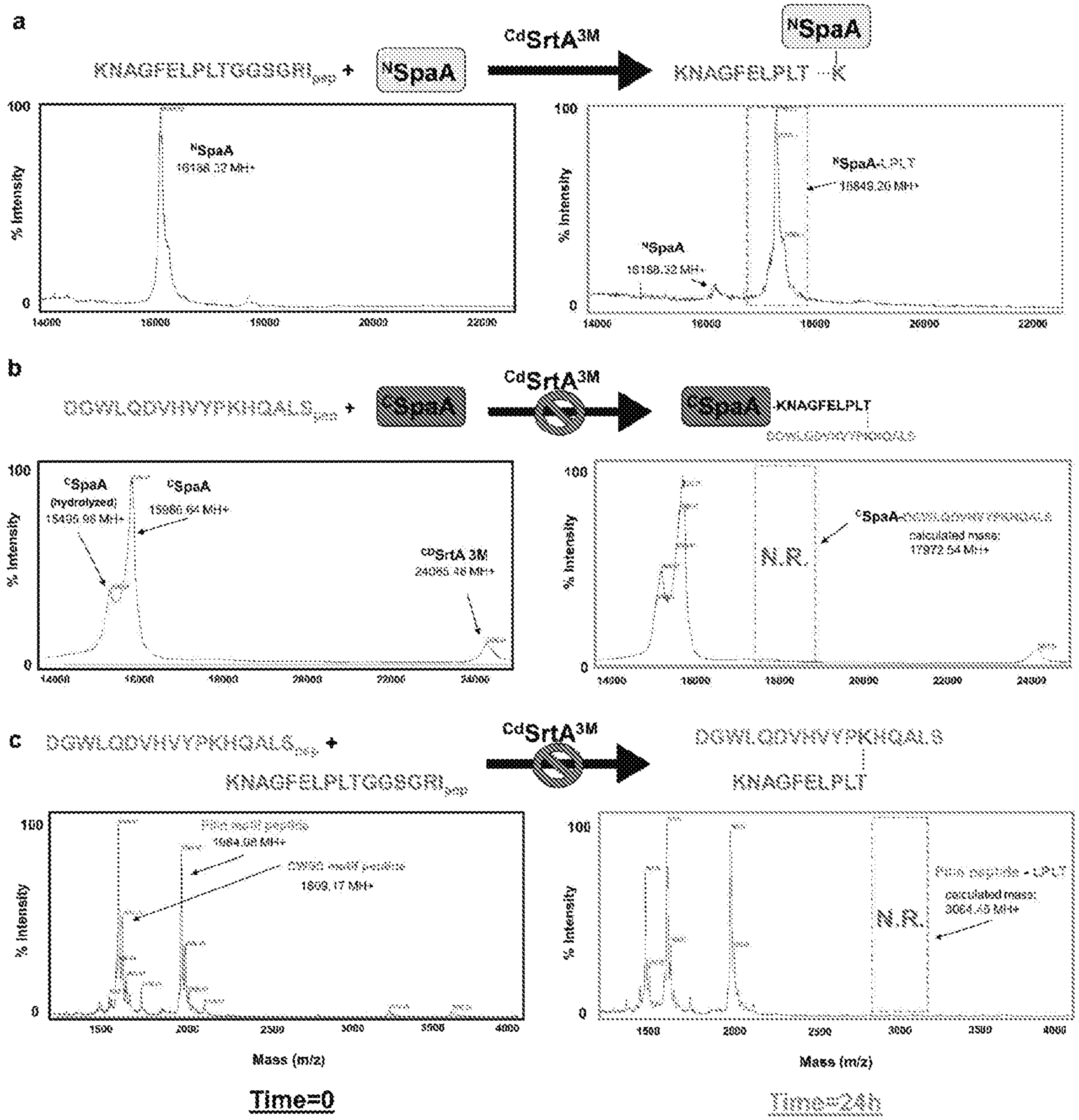
FIGS. 12A-12C: Substrate recognition determinants of CdSrtA$^{3M}$ are determined by MALDI-MS.

To elucidate determinants required for recognition of the K190 nucleophile, CdSrtA$^{3M}$ was incubated with a peptide containing the pilin motif (DGWLQDVHVYPKHQALS (SEQ ID NO. 11)) and either $^{C}$SpaA or a peptide containing its C-terminal sorting signal (KNAGFELPLTGGSGRI (SEQ ID NO. 9)) (FIG. 12). In both instances, no detectable product was observed, indicating that CdSrtA$^{3M}$ requires tertiary elements of the $^{N}$SpaA domain to recognize K190. In contrast, when CdSrtA$^{3M}$ is incubated with $^{N}$SpaA and the peptide containing the C-terminal sorting signal, >95% of $^{N}$SpaA is labeled with the peptide (FIG. 8C). Moreover, LC-MS/MS analysis of the crosslinked species reveals that is constructed from a site-specific isopeptide bond linkage between the threonine within the sorting signal peptide and the NE amine of K190 in $^{N}$SpaA (FIG. 8D).

We next demonstrated that CdSrtA$^{3M}$ can be used to label a target protein via an isopeptide bond with either a peptide fluorophore or another protein. In the labeling reaction the target protein is first expressed as a fusion with the $^{N}$SpaA domain containing the pilin motif (PM), and then reacted with a LPLTG(SEQ ID NO. 5)-containing biomolecule and CdSrtA$^{3M}$ (FIG. 9A). To demonstrate peptide fluorophore attachment with CdSrtA$^{3M}$, we incubated the enzyme with $^{N}$SpaA and a fluorescent FITC-KNAGFELPLTGGSGRI (SEQ ID NO. 9) peptide (FITCLPLTpep) and CdSrtA$^{3M}$ for 24 or 48 hours. The reaction was then separated by SDS-PAGE and visualized by either coomassie staining or FITC fluorescence at 530 nm. CdSrtA$^{3M}$ labels $^{N}$SpaA with the fluorescent peptide, yielding a FITC-LPLTx$^{N}$SpaA cross-linked product (FIG. 9B, right). Fluorophore labeling is specific, as $^{N}$SpaA harboring a K190A mutation is unreactive in control experiments (FIG. 9B, left). To demonstrate that CdSrtA$^{3M}$ can also be used to join proteins together, PM was reacted with green fluorescent protein modified at its C-terminus to contain the LPLTGGSGRI (SEQ ID NO. 15) sorting signal sequence (GFP-LPLTG). Incubation of these proteins with CdSrtA$^{3M}$ resulting in the appearance a higher molecular weight GFP-LPLTx$^{N}$SpaA cross-linked product (FIG. 9C). Notably, the CdSrtA$^{3M}$ protein-protein ligation reaction is versatile, as labeling can achieved with the $^{N}$SpaA pilin motif located at either the N- or C-terminus of the target protein. The CdSrtA$^{3M}$ catalyzed protein-protein ligation reaction is not as robust as peptide labeling with FITC-LPLTG peptide, consistent with the lower amount of the GFP-LPLTG substrate employed.

The CdSrtA and SaSrtA sortase transpeptidases recognize chemically distinct nucleophiles and sorting signals, suggesting that they can be used orthogonally to selectively label a single target protein at different sites. In the orthogonal modification strategy a target protein is produced that contains the N-terminal oligoglycine and pilin K190 nucleophiles that are recognized by SaSrtA and CdSrtA$^{3M}$, respectively. To demonstrate orthogonal labeling we created a fusion protein that contained the Small Ubiquitin-like Modifier (SUMO) protein harboring pentaglycine peptide and the pilin motif at its N- and C-termini, respectively (G5-SUMOPM). The fusion protein was then sequentially reacted with each enzyme and peptide fluorophores containing the cognate sorting signal (FIG. 10A). To selectively modify Gly5-SUMOPM (species 1), it was incubated overnight with CdSrtA$^{3M}$ and FITC-LPLTGpep to create at high yield G5-SUMOPM-FITC (species 2) (FIG. 10B). After removal of excess FITC-LPLTG peptide using a desalting column, the target protein was then labeled at its N-terminus with AlexaFlour$_{546}$-LPATG (SEQ ID NO. 5) using an activated SaSrtA enzyme. This was achieved by incubating species 2 with SaSrtA and AlexaFlour$_{546}$-LPATG (SEQ ID NO. 5) for either 0.25 or 2 hrs to produce the doubly labeled protein (species 3).

Figure 13:
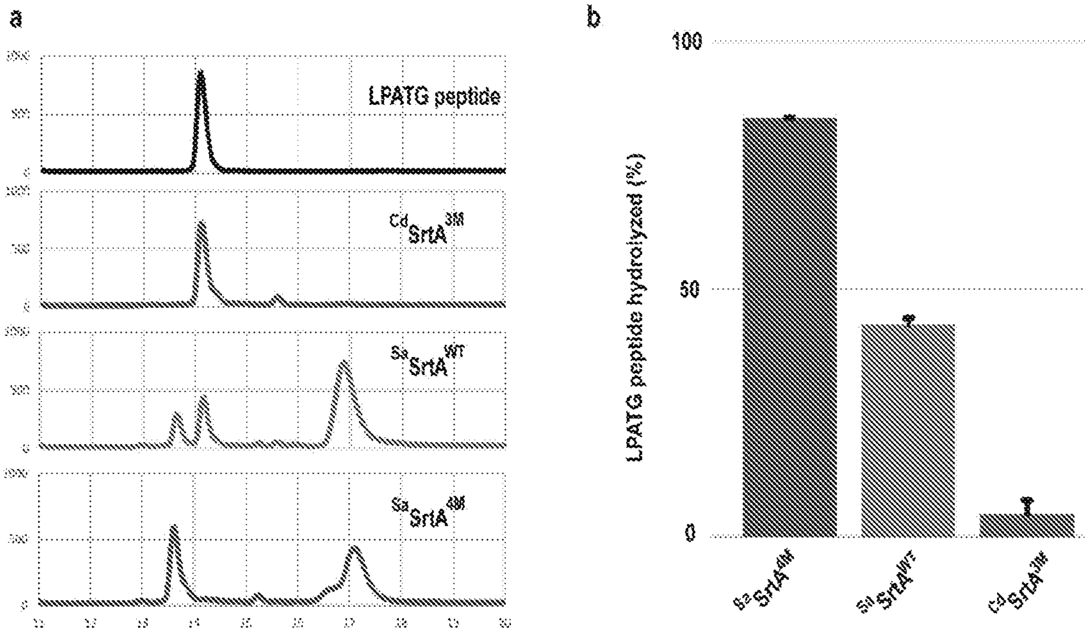
FIGS. 13A-13B: CdSrtA$^{3M}$ demonstrates uncommon specificity for leucine in the X position of the LPXTG (SEQ ID NO. 5) sorting signal. Incubation of CdSrtA$^{3M}$ and SaSrtA with a short peptide containing an LPATG motif (KNAGFELPATGGSGRI (SEQ ID NO: 9)) indicates that CdSrtA$^{3M}$ is unable to process any significant amount of peptide, while SaSrtA robustly hydrolyzes the LPATG (SEQ ID NO. 5) peptide, as expected. The improved variant, SaSrtA 4M$^{3}$, almost entirely hydrolyzes the full length peptide after 24 hrs. This data suggests CdSrtA$^{3M}$ has a strong bias for leucine in the X position of LPXTG (SEQ ID NO. 5).
Figure 14:
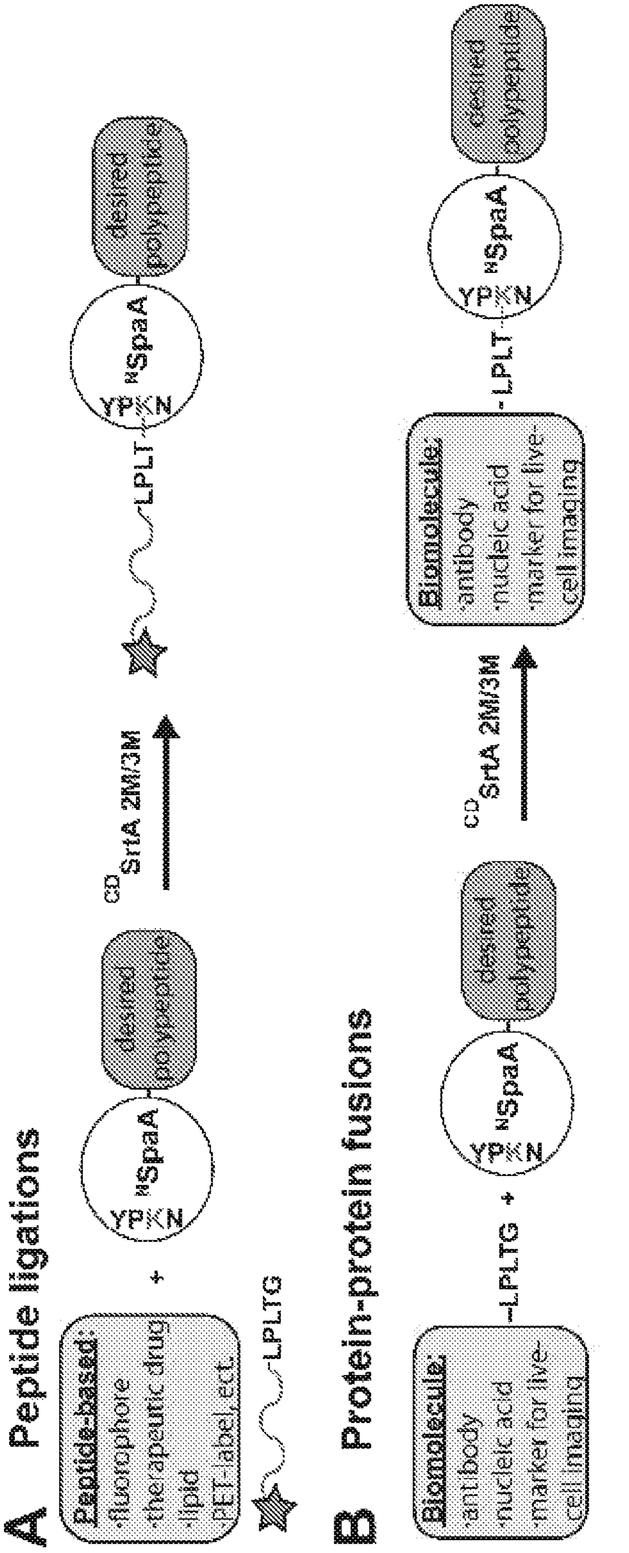
FIGS. 14A-14B: Schematic showing biocongugation reactions that can be catalyzed by the new reagent.

Separation of the reaction products by SDS-PAGE confirms dual labeling, as the appropriate fluorescence for each probe is detected during the procedure at ~33 kD (FIG. 10B). In particular, FITC labeled Gly5-SUMOPM is produced after treatment with CdSrtA$^{3M}$ (488/530 nm excitation/emission), and persists after treatment with SaSrtA that catalyzes the second conjugation containing AlexaFlour$_{546}$ (532/605 nm excitation/emission). A strength of our approach is the distinct nucleophile and sorting signal substrate specificities of each sortase, which limits cross reactivity. Notably, our findings indicate that in addition to recognizing distinct nucleophiles, the sortases show unique sorting signal specificities; CdSrtA$^{3M}$ is unable to process sorting signals containing the sequence LPATG (SEQ ID NO. 5) that are used by SaSrtA, but instead is selective for peptides containing LPLTG (SEQ ID NO. 5) (FIG. 13). Moreover, the peptide installed by CdSrtA$^{3M}$ is not vulnerable to reversal by SaSrtA due to the branched isopeptide linkage. Thus, each sortase acts exclusively on its respective substrate, ensuring specific placement on the target protein.

The bioconjugation chemistry catalyzed by CdSrtA$^{3M}$ enables site specific lysine labeling of a protein, creating isopeptide linkages that may be less susceptible to proteolysis than conventional peptide bonds. Transglutaminases also can modify protein lysine residues, but unlike CdSrtA$^{3M}$, these enzymes exhibit minimal substrate specifity[26,27]. SaSrtA can also modify lysines, but this is a side reaction that occurs with minimal specificity and at low efficiency because the lysine ε-amine is not SaSrtA's natural substrate[9,15,16]. Bioconjugation catalyzed by CdSrtA$^{3M}$ is functionally similar to the non-enzymatic SpyTag/SpyCatcher system, but it is unique because it is enzyme catalyzed and can therefore be better controlled. CdSrtA$^{3M}$ can be used in combination SaSrtA chemoenzymatic labeling, providing a new and powerful avenue for protein bioconjugation.

Protein Expression and Purification

His$^6$-tagged proteins were purified according to a published procedure. Briefly, *E. coli* BL21 (DE3) cells harboring pSUMO-CdSrtA$^{WT}$, pSUMO-CdSrtA$^{2M}$, pSUMO-CdSrtA$^{3M}$, pSUMO-SaSrtA WT, pSUMO-SaSrtA 4M, pSUMO-$^{N}$SpaA, or pSUMO-SpaA were grown in LB supplemented with kanamycin at 500 μg/ml at 37° C. until OD600 of ~0.6. Cells were induced with 1 mM IPTG and protein expression was allowed to proceed overnight at 17° C. Cells were then harvested by centrifugation (7,000 RPM for 10 min). All proteins were purified as a His6x-SUMO-fusion using HisPure Co2+ IMAC resin (Thermo) per the manufacturer's instructions. Briefly, cell pellets were resuspended in 50 mM Tris-HCl pH 8.0, 300 mM NaCl (lysis buffer) and lysed by high pressure homogenization. Subsequent cell lysate was then fractionated by centrifugation (15,000 RPM for 40 min) and the supernatant was loaded onto HisPure Co2+ IMAC resin. Proteins were then eluted from the resin using lysis buffer supplemented with 200 mM Imidazole. The His6x-SUMO tag was removed by the addition of His6x-Ulp1 protease, and subsequent HisPure Co2+ purification. Protein purity was determined by SDS-PAGE analysis.

In Vitro of Pilin Domain Coupling Assays

In vitro reactions were carried out at room temperature and proteins were dissolved in assay buffer (50 mM Tris-HCl pH 8.0, 300 mM NaCl, 5 mM DTT). All reactions used a fixed 100 μM concentration of SrtA enzyme and 300 μM SpaA substrate (SpaA and $^{N}$SpaA). Reactions were stirred gently by continuous rotation. Time points were taken at 0 h, 24 h, 48 h and reactions were quenched by addition of two volumes of SDS-loading dye. Quantitative analysis of transpeptidation was carried out by analyzing band intensities of the gel images using ImageJ (NIH)2.

Sortase-Catalyzed Peptide Conjugation Reactions

In general, 100 μM CdSrtA$^{3M}$ was incubated with 1 mM peptide and 100 μM of the pilin domain ($^{N}$SpaA or SpaA) in 50 μl reactions, in the presence of 5 mM DTT for 24 hours. For SaSrtA mediated peptide conjugation, the improved variant "4M" (bearing the following point mutations: P94S/D160N/D165A/K196T) was used to improve transpeptidation speed[3]. 15 minutes incubation with 25 μM SaSrtA 4M resulted in partial labeling, and extended incubation of 2 hours yields almost complete labeling. After the incubations, the reactions were diluted 10× with ddH2O and mixed with 2,5 dihydroxybenzoic acid matrix (DHB) for analysis by matrix-assisted laser desorption ionization mass spectrometry (MALDI) or diluted with 25 μl SDS and separated by SDS-PAGE for further analysis.

Determination of SrtA Hydrolysis by an HPLC-Based Assay

In vitro hydrolysis reactions were performed based on the method developed by Kruger et al[4]. The sorting signal peptide was synthesized by Peptide2.0 and used without further purification. Lyophilized peptide was dissolved in assay buffer to 2 mM. 50 μM CdSrtA or SaSrtA (wild-type or mutant) was incubated with 500 μM KNAGFELPLTGGSGRI (SEQ ID NO. 9) (LPLTGpep) or KNAGFELPATGGSGRI (SEQ ID NO. 17) (LPATGpep) and 5 mM DTT in 100 μl reactions at 37° C. for 24 h and 48h. The reactions were quenched by adding 50 μl of 1 M HCl and injected onto a Waters)(Bridge Peptide BEH C18 reversed phase HPLC column. Peptides were eluted by applying a gradient from 5 to 51% acetonitrile (in 0.1% trifluoroacetic acid) over 30 minutes at a flow rate of 1 ml/min. Elution of the peptides was monitored by absorbance at 215 nm. Quantitative analysis of the HPLC traces was facilitated by integration of individual peak areas using Graphical Analysis (Vernier).

Fluorescent Peptides and Fluorescent Gel Imaging

FITC-KNAGFELPLTGGSGRI (SEQ ID NO. 9) was synthesized by Peptide 2.0 and used without further purification. AlexaFluor$_{546}$-CNAGFELPATGGSRI (SEQ ID NO. 18) was created by expressing Psumo-CNAGFELPATGGSRI (SEQ ID NO. 18) in BL21 (DE3) cells and purifying the His-tagged fusion protein by Co2+ IMAC, as described previously. The desired peptide was cleaved from SUMO by treating with His6x-ULP1 protease and the peptide was purified by an additional Co2+ IMAC purification. The resultant peptide was then reduced with 1 mM TCEP and selectively modified by AlexaFluor$_{546}$-maliemide (Invitrogen) via the N-terminal cysteine residue on the peptide. The fluorescent peptide was purified again by separation with a Waters XSelect HSS C18 reversed phase HPLC column. The fluorescent peptide conjugate was confirmed by absorbance at 554 nm and MALDI and lyophilized. Both peptides were dissolved into assay buffer at 2 mM. Sortase-catalyzed peptide modifications were performed as described, and samples were loaded onto pre-cast 12% linear Bis-Tris NuPAGE gels and run at 170V for 70 min to achieve separation between apo $^{N}$SpaA and $^{N}$SpaA modified by LPLTGpep. The gels were then washed in ddH2O and fluorescence data was acquired with a Pharos FX gel imager (BioRad). Fluorescein isothiocyanate (FITC) was detected by excitation with a 488 nm laser line and detection with a 515-545 nm emission filter. AlexaFluor$_{546}$ was detected by excitation with a 532 nm laser line and detection by an emission filter at 580-630 nm.

Tandem Mass Spectrometry of $^{N}$SpaA-LPLTpep Complex

Protein digestion and isopeptide bond identification were performed according to previous protocols. Specifically, proteins entrapped in gel bands were reduced with 10 mM dithiothreitol (Sigma) at 60° C. for an hour and then alkylated with 50 mM iodoacetamide (Sigma) at 45° C. for a few minutes in the dark. These reduction and alkylation steps were skipped for the acyl intermediate samples. Samples were digested with 200 ng trypsin (Thermo Scientific) at 37° C. overnight. At the end of trypsin digestion, 200 ng of Asp-N endoproteinase (Thermo Scientific) were added for another overnight incubation. Digested peptides were extracted from the gel bands in 50% acetonitrile/49.9% water/0.1% trifluoroacetic acid (TFA) and cleaned with C18 StageTip before mass spectrometry analysis.

Digested peptides were separated on EASY-Spray column (25 cm×75 μm ID, PepMap RSLC C18, 2 μm, Thermo Scientific) connected to an EASY-nLC 1000 nUPLC (Thermo Scientific) using a gradient of 5-35% acetonitrile in 0.1% formic acid and a flow rate of 300 nl/min for 30 minutes. Tandem mass spectra were acquired in a data-dependent manner with an Orbitrap Q Exactive mass spectrometer (Thermo Fisher Scientific) interfaced to a nano-electrospray ionization source.

The raw MS/MS data were converted into MGF format by Thermo Proteome Discoverer 1.4 (Thermo Scientific). We wrote in-house programs to search for the isopeptides in two different approaches. The first approach was performed as previously described and used calculated masses of predicted peptides containing the isopeptide linkage to guide the search. The second approach was based on the observation of published spectra as well as our own on the presence of ions specific for the fragments of ELPLT (m/z 215.138, 225.122, 243.132, 294.180, 312.190, 322.174 and 340.186). The in-house programs sifted through tens of thousands of mass spectra looking for this information specifically and pulled out mass spectra of interest for further analysis and manual validation.

EXAMPLE 2 REFERENCES

1. Mazmanian, S. K. *Staphylococcus aureus* Sortase, an Enzyme that Anchors Surface Proteins to the Cell Wall. *Science* (80-.). 285, 760-763 (1999).
2. Antos, J. M. et al. Site-specific N- and C-terminal labeling of a single polypeptide using sortases of different specificity. *J. Am. Chem. Soc.* 131, 10800-10801 (2009).
3. Williamson, D. J., Fascione, M. A., Webb, M. E. & Turnbull, W. B. Efficient N-terminal labeling of proteins by use of sortase. *Angew. Chemie-Int. Ed.* 51, 9377-9380 (2012).
4. Levary, D. A., Parthasarathy, R., Boder, E. T. & Ackerman, M. E. Protein-Protein Fusion Catalyzed by Sortase A. *PLoS One* 6, (2011).
5. Popp, M. W., Antos, J. M., Grotenbreg, G. M., Spooner, E. & Ploegh, H. L. Sortagging: A versatile method for protein labeling. *Nat. Chem. Biol.* 3, 707-708 (2007). 6. Mao, H., Hart, S. A., Schink, A. & Pollok, B. A. Sortase-Mediated Protein Ligation: A New Method for Protein Engineering. *J. Am. Chem. Soc.* 126, 2670-2671 (2004).
7. Samantaray, S., Marathe, U., Dasgupta, S., Nandicoori, V. K. & Roy, R. P. Peptide-sugar ligation catalyzed by transpeptidase sortase: A facile approach to neoglycoconjugate synthesis. *J. Am. Chem. Soc.* 130, 2132-2133 (2008).
8. Antos, J. M., Miller, G. M., Grotenbreg, G. M. & Ploegh, H. L. Lipid modification of proteins through sortase-catalyzed transpeptidation. *J. Am. Chem. Soc.* 130, 16338-16343 (2008).
9. Möhlmann, S., Mahlert, C., Greven, S., Scholz, P. & Harrenga, A. In vitro Sortagging of an Antibody Fab Fragment: Overcoming Unproductive Reactions of Sortase with Water and Lysine Side Chains. *ChemBioChem* 12, 1774-1780 (2011).
10. Wagner, K. et al. Bispecific antibody generated with sortase and click chemistry has broad antiinfluenza virus activity. *Proc. Natl. Acad. Sci.* 111, 16820-16825 (2014).
11. Beerli, R. R., Hell, T., Merkel, A. S. & Grawunder, U. Sortase enzyme-mediated generation of site-specifically conjugated antibody drug conjugates with high In Vitro and In Vivo potency. *PLoS One* 10, (2015).
12. Amer, B. R., MacDonald, R., Jacobitz, A. W., Liauw, B. & Clubb, R. T. Rapid addition of unlabeled silent solubility tags to proteins using a new substrate-fused sortase reagent. *J. Biomol. NMR* 64, 197-205 (2016).
13. Dorr, B. M., Ham, H. O., An, C., Chaikof, E. L. & Liu, D. R. Reprogramming the specificity of sortase enzymes. *Proc. Natl. Acad. Sci.* 111, 13343-13348 (2014).
14. Chen, I., Dorr, B. M. & Liu, D. R. A general strategy for the evolution of bond-forming enzymes using yeast display. *Proc. Natl. Acad. Sci.* 108, 11399-11404 (2011).
15. Dasgupta, S., Samantaray, S., Sahal, D. & Roy, R. P. Isopeptide ligation catalyzed by quintessential sortase A: Mechanistic cues from cyclic and branched oligomers of indolicidin. *J. Biol. Chem.* 286, 23996-24006 (2011).
16. Bellucci, J. J., Bhattacharyya, J. & Chilkoti, A. A noncanonical function of sortase enables site-specific conjugation of small molecules to lysine residues in proteins. *Angew. Chemie-Int. Ed.* 54, 441-445 (2015).
17. Danne, C. & Dramsi, S. Pili of Gram-positive bacteria: roles in host colonization. *Res. Microbiol.* 163, 645-658 (2012).
18. Spirig, T., Weiner, E. M. & Clubb, R. T. Sortase enzymes in Gram-positive bacteria. *Mol. Microbiol.* 82, 1044-1059 (2011).
19. Ton-That, H. & Schneewind, O. Assembly of pili in Grampositive bacteria. *Trends in Microbiology* 12, 228-234 (2004).

20. Chang, C. et al. In vitro reconstitution of sortase-catalyzed pilus polymerization reveals structural elements involved in pilin crosslinking. *Proc. Natl. Acad. Sci*. (In revision) (2018).

21. Jacobitz, A. W. et al. The 'Lid' in the *Streptococcus pneumoniae* SrtC1 Sortase Adopts a Rigid Structure that Regulates Substrate Access to the Active Site. *J. Phys. Chem. B* acs.jpcb.6b01930 (2016). doi:10.1021/acs.jpcb.6b01930

22. Manzano, C., Izoré, T., Job, V., Di Guilmi, A. M. & Dessen, A. Sortase Activity Is Controlled by a Flexible Lid in the Pilus Biogenesis Mechanism of Gram-Positive Pathogens, Biochemistry 48, 10549-10557 (2009).

23. Cozzi, R. et al. Group B *Streptococcus* pillus sortase regulation: A single mutation in the lid region induces pilin protein polymerization in vitro. *FASEB J.* 27, 3144-3154 (2013).

24. Persson, K. Structure of the sortase AcSrtC-1 from *Actinomyces* oris. *Acta Crystallogr*. Sect. *D Biol. Crystallogr* 67, 212-217 (2011).

25. Manzano, C. et al. Sortase-Mediated Pilus Fiber Biogenesis in *Streptococcus pneumoniae*. Structure 16, 1838-1848 (2008).

26. Yokoyama, K., Nio, N. & Kikuchi, Y. Properties and applications of microbial transglutaminase. *Applied Microbiology and Biotechnology* 64, 447-454 (2004).

27. Folk, J. E. Mechanism and basis for specificity of transglutaminase-catalyzed ε-(γ-glutamyl) lysine bond formation. *Adv. Enzymol. Relat. Areas Mol. Biol.* 54, 1-56 (1983).

28. Veggiani, G., Zakeri, B. & Howarth, M. Superglue from bacteria: Unbreakable bridges for protein nanotechnology. *Trends in Biotechnology* 32, 506-512 (2014).

Polypeptide and Polynucleotide Sequences

*Corynebacterium diphtheriae* CdSrtA (active truncated variant sequence with lid residues underlined):
NNARQARVAQSYENSYEVDSPAVRDSVLEAARQYNTSVVGFPILDPWLNRASKNS
GPYLDYLQQLNPQRAERPVIASISIPTIDAHLPIYHGTDTATLEHGLGHLYGSALPV
GGTGTHPVITGHSGLANATLFDNLEDVKFHDPIYITVQGETLKYEVDAINVVLPE
DTKILAPDPNKDQITLITCTPYAVNSHRLLVRAHRVDLDPNDPNLTQTGTKIWQ
(SEQ ID NO: 1)

*Corynebacterium diphtheriae* CdSrtA variant of SEQ ID NO. 1 (active truncated variant sequence deleting lid residues "ILGPGLNRA"):
NNARQARVAQSYENSYEVDSPAVRDSVLEAARQYNTSVVGFPSKNSGPYLDYLQ
QLNPQRAERPVIASISIPTIDAHLPIYHGTDTATLEHGLGHLYGSALPVGGTGTHP
VITGHSGLANATLFDNLEDVKFHDPIYITVQGETLKYEVDAINVVLPEDTKILAP
DPNKDQITLITCTPYAVNSHRLLVRAHRVDLDPNDPNLTQTGTKIWQ (SEQ ID
NO: 40)

Wild type *Corynebacterium diphtheriae* SrtA ("DPW" lid residues highlighted)
MRHRAGEHRNVFAILAFVIAIVSVGFLLYPVAATAWNNARQARVAQSYENSYEVD
SPAVRDSVLEAARQYNTSVVGFPILDPWLNRASKNSGPYLDYLQQLNPQRAERPVI
ASISIPTIDAHLPIYHGTDTATLEHGLGHLYGSALPVGGTGTHPVITGHSGLANAT
LFDNLEDVKFHDPIYITVQGETLKYEVDAINVVLPEDTKILAPDPNKDQITLITCT
PYAVNSHRLLVRAHRVDLDPNDPNLTQTGTKIWQPWMLWTAALALTAIAIIITLV
LRRKRTTTHEK (SEQ ID NO: 41)

*Staphylococcus aureus* Sortase
GenBank LOCUS: ELP27013.1
MKKWTNRLMTIAGVVLILVAAYLFAKPHIDNYLHDKDKDEKIEQYDKNVKEQA
SKDKKQQAKPQIPKDKSKVAGYIEIPDADIKEPVYPGPATPEQLNRGVSFAEENES
LDDQNISIAGHTFIDRPNYQFTNLKAAKKGSMVYFKVGNETRKYKMTSIRDVKP
TDVGVLDEQKGKDKQLTLITCDDYNEKTGVWEKRKIFVATEVK (SEQ ID NO: 2)

*Corynebacterium Diphtheriae* Major Pilin SpaA
LOCUS: 3HR6_A 436 aa
REFERENCE: Kang et al., Proc. Natl. Acad. Sci. U.S.A. 106 (40), 16967-16971 (2009)
GPERTSIAVHALMGLPTGQPANGTKLDSIGLPKVDGMSFTLYRVNEIDLTTQAG
WDAASKIKLEELYTNGHPTDKVTKVATKKTEGGVAKFDNLTPALYLVVQELNG
AEAVVRSQPFLVAAPQTNPTGDGWLQDVHVYPKHQALSEPVKTAVDPDATQPG
FSVGENVKYRVATKIPEIASNTKFEGFTVADKLPAELGKPDTNKITVTLGGKPINS
TDVSVQTYQVGDRTVLSVQLAGATLQSLDQHKDQELVVEFEAPVTKQPENGQL
DNQAWVLPSNPTAQWDPEESGDAALRGMPSSRVSSKFGQITIEKSFDGNTPGAD
RTATFQLHRCEADGSLVKSDPPISLDGKQEFVTGQDGKAVLSGIHLGTLQLESNV
MKYTDAWAGKGTEFCLVETATASGYELLPKPVIVKLEANESTNVLVEQKVKIDN
KKKN (SEQ ID NO: 3)

*Corynebacterium diphtheriae* surface-anchored fimbrial subunit SpaB
LOCUS VEJ64585 209 aa
MKNNAINATVLSFALIIGTTPAHAQETNTLVIDLEPPAAFADDQPQGHNIDVTVTR
LHNIDPQDHERIRDLQRNGVPNTISEEQLHTARTDATGTATITNLPPGAYVIRDSN
TTKPRFSPLVIPLGIDTTSPTMTLRPKLIDVTPGAPNVPSTPSVPSPPSATASAPAKK
TPPRLAFTGASILGLLAIATISTLIGIALIRTRRAENKG (SEQ ID NO: 4)

-continued

TABLE 1

Sequence alignment of Gram-positive sortases showing the class C signature sequence. Shown is an alignment of amino acids encompassing strands β7 to β8 of class C sortases. All aligned class C enzymes have been experimentally demonstrated to assemble pili by either cellular or biochemical methods. The conserved TP(Y/L)XIN(S/T)H (SEQ ID NO: 10) signature sequence in class C enzymes is shaded in light blue, while the catalytic cysteine and arginine residues are colored red. The bottom of the table shows representative class A, B, D and E enzymes sortases that do not assemble pili, but instead attach proteins to the cell wall. The GenBank accession codes are as follows: WP_010935503 (*Corynebacterium diphtheriae* SrtA); WP_010934130 (*Corynebacterium diphtheriae* SrtB); WP_010934133 (*Corynebacterium diphtheriae* SrtC); WP_010935679 (*Corynebacterium diphtheriae*, SrtD); WP_010935678 (*Corynebacterium diphtheriae*, SrtE); WP_002307920 (*Enterococcus faecium*, SrtC); WP_014569086 (*Lactobacillus rhamnosus*, SrtC1); WP_060958109 (*Actinomyces oris*, SrtC1); WP_060956887 (*Actinomyces oris*, SrtC2); WP_000047114 (*Streptococcus pneumoniae*, SrtC 1); WP_050148456 (*Streptococcus agalactiae*, SrtC 1); WP_000746885 (*Streptococcus agalactiae*, SrtC2); WP_000828081 (*Bacillus cereus*, SrtD); WP_037276992 (*Ruminococcus albus*,SrtC).

| CLASS A | | |
|---|---|---|
| *Corynebacterium diphtheriae* SrtA | DPNKD-QITLITCTPYAVNSH----R-LLVRAHRVDL | (SEQ ID NO. 20) |
| *Corynebacterium diphtheriae* SrtC | EQGKD-YITLITCTPYGINTH----R-LMVRGHQVPL | (SEQ ID NO. 21) |
| *Corynebacterium diphtheriae* SrtB | TSNKD-QVTLITCTPYGINTH----R-LIITAERVPM | (SEQ ID NO. 22) |
| *Corynebacterium diphtheriae* SrtD | QDDRD-LVTLVTCTPLGINTH----R-ILVTAERITP | (SEQ ID NO. 23) |
| *Corynebacterium diphtheriae* SrtE | IPDRD-LITLVTCTPYGINTH----R-LLVTAERVPM | (SEQ ID NO. 24) |
| *Lactobacillus rhamnosus* SrtC1 | VPGQD-LVTLMTCTPYMINSH----R-LLITGRRIPY | (SEQ ID NO. 25) |
| *faecium* class C sortase 1 | SEGED-LVTLLTCTPYMINTH----R-LLVTGHRIPY | (SEQ ID NO. 26) |
| *faecium* class C sortase 2 | EKGQD-FVTLLTCTPYMVNSH----R-LLVRGHRVPY | (SEQ ID NO. 27) |
| SrtC1 | EEGKD-LLTLVTCTPLGINTH----R-ILLTGERIYP | (SEQ ID NO. 28) |
| *Actinomyces oris* SrtC2 | VPGRD-LVTLITCTPYGVNSH----R-LLVTGERVPM | (SEQ ID NO. 29) |
| *Streptococcus pneumoniae* SrtC1 | QHGED-YATLLTCTPYMINSH----R-LLVRGKRIPY | (SEQ ID NO. 30) |
| *Streptococcus agalactiae* SrtC1 | IQGED-HVTLLTCTPYMINSH----R-LLVRGKRIPY | (SEQ ID NO. 31) |
| *Streptococcus agalactiae* SrtC2 | VNGKD-YITLLTCTPYMINSH----R-LLVKGERIPY | (SEQ ID NO. 32) |
| *Bacillus cereus* SrtD | VQNKD-YTTLITCTPYGINTN----R-LLVRGERVEL | (SEQ ID NO. 33) |
| *Ruminococcus albus* class C sortase | IPNED-EVTLMTCTPYGINTH----R-LLIRAHRIKS | (SEQ ID NO. 34) |
| CLASS A, B, D, E AND E | | |
| *Staphylococcus aureus* SrtA | QKGKDKQLTLITCDDYNEKTGVWEKRKIFVATEVK-- | (SEQ ID NO. 35) |
| *Streptococcus pyogenes* SrtB | KHHTK-FVAFSTCENFST-----DNR-VIVVGTIQEI | (SEQ ID NO. 36) |
| *Clostridium perfringens* SrtD | -----KTMTIVTCTNRGK------DR-YIVKAKLIG | (SEQ ID NO. 37) |
| *Streptomyces coelicolor* | FKGPGRYITLTTCTPEFTSKY----R-MIVWGKMVEE | (SEQ ID NO. 38) |
| *Corynebacterium diphtheriae* SrtF | DPGMEGIMTMTTCHPQFSNA----ER-MIVHAMLTEH | (SEQ ID NO. 39) |

TABLE 2

Kinetic Parameters of sortase variants

| | 3M | Δ |
|---|---|---|
| $K_m$ (M) × $10^{-4}$ | 0.8 ± 0.1 | 1.6 ± 0.4 |
| $V_{max}$ ($s^{-1}$) × $10^{-9}$ | 1.4 ± 0.2 | 10.0 ± 2.0 |
| $k_{cat}$ ($s^{-1}$) × $10^{-5}$ | 5.7 ± 0.8 | 40.0 ± 9.0 |
| $k_{cat}/k_M$($s^{-1}$/M) | 0.7 ± 0.1 | 2.5 ± 0.6 |

Embodiments and aspects of the present invention disclosed herein were found in manuscript disclosure that was included with the priority application disclosure (U.S. Provisional Patent Application Ser. No. 62/665,076, filed on May 1, 2018) before the manuscripts were published. The manuscripts were later published as Chang et al., PNAS Jun. 12, 2018 115 (24) E5477-E5486 and McConnell et al., J. Am. Chem. Soc., 2018, 140 (27), pp 8420-8423.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

CONCLUSION

This concludes the description of the illustrative embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A method of forming an isopeptide bond in vitro between a threonine residue in a first polypeptide and a lysine residue in a second polypeptide, the method comprising:

forming a mixture comprising the first polypeptide and the second polypeptide disposed within a composition comprising:

a *Corynebacterium diphtheriae* Class C sortase variant polypeptide having at least 90% identity and an amino acid substitution of D45G, W47G and/or N49A in SEQ ID NO: 1, wherein the *Corynebacterium diphtheriae* Class C sortase variant polypeptide exhibits an increased ability to catalyze threonine-lysine isopeptide bond formation in vitro as compared to a wild type *Corynebacterium diphtheriae* Class C sortase;

allowing the *Corynebacterium diphtheriae* Class C sortase variant polypeptide to form an isopeptide bond between the threonine residue in the first polypeptide and the lysine residue in the second polypeptide.

2. The method of claim 1, wherein the first polypeptide comprises an amino acid motif containing SEQ ID NO: 3 or SEQ ID NO: 4.

3. The method of claim 2, wherein the *Corynebacterium diphtheriae* Class C sortase variant polypeptide comprises substitution mutations D45G and W47G in SEQ ID NO:1.

4. The method of claim 3, wherein the variant polypeptide further comprises *Corynebacterium diphtheriae* Class C sortase variant polypeptide further comprises mutation N49A in SEQ ID NO: 1.

5. The method of claim 1, wherein a polypeptide in the mixture comprises a detectable marker, an antibody, a growth factor or a fluorescent protein.

6. The method of claim 5, wherein the detectable marker comprises a fluorophore or a Positron Emission Tomography (PET) label.

7. The method of claim 1, wherein the mixture further comprises an excipient selected from the group consisting of: a preservative, a tonicity adjusting agent, a detergent, a viscosity adjusting agent, a sugar or a pH adjusting agent.

8. A method of forming an isopeptide bond in vitro between a threonine residue in a first polypeptide and a lysine residue in a second polypeptide, the method comprising:

forming a mixture comprising the first polypeptide and the second polypeptide disposed within a composition comprising:

a *Corynebacterium diphtheriae* Class C sortase variant polypeptide having at least 90% identity and an amino acid substitution of D45G in SEQ ID NO: 1, wherein the *Corynebacterium diphtheriae* Class C sortase variant polypeptide exhibits an increased ability to catalyze threonine-lysine isopeptide bond formation in vitro as compared to a wild type *Corynebacterium diphtheriae* Class C sortase;

allowing the *Corynebacterium diphtheriae* Class C sortase variant polypeptide to form an isopeptide bond between the threonine residue in the first polypeptide and the lysine residue in the second polypeptide.

9. A method of forming an isopeptide bond in vitro between a threonine residue in a first polypeptide and a lysine residue in a second polypeptide, the method comprising:

forming a mixture comprising the first polypeptide and the second polypeptide disposed within a composition comprising:

a *Corynebacterium diphtheriae* Class C sortase variant polypeptide having at least 90% identity and an amino acid substitution of W47G in SEQ ID NO: 1, wherein the *Corynebacterium diphtheriae* Class C sortase variant polypeptide exhibits an increased ability to catalyze threonine-lysine isopeptide bond formation in vitro as compared to a wild type *Corynebacterium diphtheriae* Class C sortase;

allowing the *Corynebacterium diphtheriae* Class C sortase variant polypeptide to form an isopeptide bond between the threonine residue in the first polypeptide and the lysine residue in the second polypeptide.

10. A method of forming an isopeptide bond in vitro between a threonine residue in a first polypeptide and a lysine residue in a second polypeptide, the method comprising:

forming a mixture comprising the first polypeptide and the second polypeptide disposed within a composition comprising:

a *Corynebacterium diphtheriae* Class C sortase variant polypeptide having at least 90% identity and an amino acid substitution of N49A in SEQ ID NO: 1, wherein the *Corynebacterium diphtheriae* Class C sortase variant polypeptide exhibits an increased ability to catalyze threonine-lysine isopeptide bond formation in vitro as compared to a wild type *Corynebacterium diphtheriae* Class C sortase;

allowing the *Corynebacterium diphtheriae* Class C sortase variant polypeptide to form an isopeptide bond between the threonine residue in the first polypeptide and the lysine residue in the second polypeptide.

* * * * *

SEQUENCE LISTING

```
<160> NUMBER OF SEQ ID NOS: 41

<210> SEQ ID NO 1
<211> LENGTH: 221
<212> TYPE: PRT
<213> ORGANISM: Corynebacterium diphtheriae

<400> SEQUENCE: 1

Asn Asn Ala Arg Gln Ala Arg Val Ala Gln Ser Tyr Glu Asn Ser Tyr
1               5                   10                  15

Glu Val Asp Ser Pro Ala Val Arg Asp Ser Val Leu Glu Ala Ala Arg
            20                  25                  30

Gln Tyr Asn Thr Ser Val Val Gly Phe Pro Ile Leu Asp Pro Trp Leu
        35                  40                  45

Asn Arg Ala Ser Lys Asn Ser Gly Pro Tyr Leu Asp Tyr Leu Gln Gln
    50                  55                  60

Leu Asn Pro Gln Arg Ala Glu Arg Pro Val Ile Ala Ser Ile Ser Ile
65                  70                  75                  80

Pro Thr Ile Asp Ala His Leu Pro Ile Tyr His Gly Thr Asp Thr Ala
                85                  90                  95

Thr Leu Glu His Gly Leu Gly His Leu Tyr Gly Ser Ala Leu Pro Val
            100                 105                 110

Gly Gly Thr Gly Thr His Pro Val Ile Thr Gly His Ser Gly Leu Ala
        115                 120                 125

Asn Ala Thr Leu Phe Asp Asn Leu Glu Asp Val Lys Glu His Asp Pro
    130                 135                 140

Ile Tyr Ile Thr Val Gln Gly Glu Thr Leu Lys Tyr Glu Val Asp Ala
145                 150                 155                 160

Ile Asn Val Val Leu Pro Glu Asp Thr Lys Leu Leu Ala Pro Asp Pro
                165                 170                 175

Asn Lys Asp Gln Ile Thr Leu Ile Thr Cys Thr Pro Tyr Ala Val Asn
            180                 185                 190

Ser His Arg Leu Leu Val Arg Ala His Arg Val Asp Leu Asp Pro Asn
        195                 200                 205

Asp Pro Asn Leu Thr Gln Thr Gly Thr Lys Ile Trp Gln
    210                 215                 220


<210> SEQ ID NO 2
<211> LENGTH: 206
<212> TYPE: PRT
<213> ORGANISM: Staphylococcus aureus

<400> SEQUENCE: 2

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30
```

-continued

```
Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205


<210> SEQ ID NO 3
<211> LENGTH: 436
<212> TYPE: PRT
<213> ORGANISM: Corynebacterium diphtheriae

<400> SEQUENCE: 3

Gly Pro Glu Arg Thr Ser Ile Ala Val His Ala Leu Met Gly Leu Pro
1               5                   10                  15

Thr Gly Gln Pro Ala Asn Gly Thr Lys Leu Asp Ser Ile Gly Leu Pro
            20                  25                  30

Lys Val Asp Gly Met Ser Phe Thr Leu Tyr Arg Val Asn Glu Ile Asp
        35                  40                  45

Leu Thr Thr Gln Ala Gly Trp Asp Ala Ala Ser Lys Ile Lys Leu Glu
    50                  55                  60

Glu Leu Tyr Thr Asn Gly His Pro Thr Asp Lys Val Thr Lys Val Ala
65                  70                  75                  80

Thr Lys Lys Thr Glu Gly Gly Val Ala Lys Phe Asp Asn Leu Thr Pro
                85                  90                  95

Ala Leu Tyr Leu Val Val Gln Glu Leu Asn Gly Ala Glu Ala Val Val
            100                 105                 110

Arg Ser Gln Pro Phe Leu Val Ala Ala Pro Gln Thr Asn Pro Thr Gly
        115                 120                 125

Asp Gly Trp Leu Gln Asp Val His Val Tyr Pro Lys His Gln Ala Leu
    130                 135                 140

Ser Glu Pro Val Lys Thr Ala Val Asp Pro Asp Ala Thr Gln Pro Gly
145                 150                 155                 160

Phe Ser Val Gly Glu Asn Val Lys Tyr Arg Val Ala Thr Lys Ile Pro
                165                 170                 175

Glu Ile Ala Ser Asn Thr Lys Phe Glu Gly Phe Thr Val Ala Asp Lys
            180                 185                 190
```

-continued

```
Leu Pro Ala Glu Leu Gly Lys Pro Asp Thr Asn Lys Ile Thr Val Thr
        195                 200                 205

Leu Gly Gly Lys Pro Ile Asn Ser Thr Asp Val Ser Val Gln Thr Tyr
    210                 215                 220

Gln Val Gly Asp Arg Thr Val Leu Ser Val Gln Leu Ala Gly Ala Thr
225                 230                 235                 240

Leu Gln Ser Leu Asp Gln His Lys Asp Gln Glu Leu Val Val Glu Phe
                245                 250                 255

Glu Ala Pro Val Thr Lys Gln Pro Glu Asn Gly Gln Leu Asp Asn Gln
            260                 265                 270

Ala Trp Val Leu Pro Ser Asn Pro Thr Ala Gln Trp Asp Pro Glu Glu
        275                 280                 285

Ser Gly Asp Ala Ala Leu Arg Gly Met Pro Ser Ser Arg Val Ser Ser
    290                 295                 300

Lys Phe Gly Gln Ile Thr Ile Glu Lys Ser Phe Asp Gly Asn Thr Pro
305                 310                 315                 320

Gly Ala Asp Arg Thr Ala Thr Phe Gln Leu His Arg Cys Glu Ala Asp
                325                 330                 335

Gly Ser Leu Val Lys Ser Asp Pro Pro Ile Ser Leu Asp Gly Lys Gln
            340                 345                 350

Glu Phe Val Thr Gly Gln Asp Gly Lys Ala Val Leu Ser Gly Ile His
        355                 360                 365

Leu Gly Thr Leu Gln Leu Glu Ser Asn Val Met Lys Tyr Thr Asp Ala
    370                 375                 380

Trp Ala Gly Lys Gly Thr Glu Phe Cys Leu Val Glu Thr Ala Thr Ala
385                 390                 395                 400

Ser Gly Tyr Glu Leu Leu Pro Lys Pro Val Ile Val Lys Leu Glu Ala
                405                 410                 415

Asn Glu Ser Thr Asn Val Leu Val Glu Gln Lys Val Lys Ile Asp Asn
            420                 425                 430

Lys Lys Lys Asn
        435


<210> SEQ ID NO 4
<211> LENGTH: 209
<212> TYPE: PRT
<213> ORGANISM: Corynebacterium diphtheriae

<400> SEQUENCE: 4

Met Lys Asn Asn Ala Ile Asn Ala Thr Val Leu Ser Phe Ala Leu Ile
1               5                   10                  15

Ile Gly Thr Thr Pro Ala His Ala Gln Glu Thr Asn Thr Leu Val Ile
            20                  25                  30

Asp Leu Glu Pro Pro Ala Ala Phe Ala Asp Asp Gln Pro Gln Gly His
        35                  40                  45

Asn Ile Asp Val Thr Val Thr Arg Leu His Asn Ile Asp Pro Gln Asp
    50                  55                  60

His Glu Arg Ile Arg Asp Leu Gln Arg Asn Gly Val Pro Asn Thr Ile
65                  70                  75                  80

Ser Glu Glu Gln Leu His Thr Ala Arg Thr Asp Ala Thr Gly Thr Ala
                85                  90                  95

Thr Ile Thr Asn Leu Pro Pro Gly Ala Tyr Val Ile Arg Asp Ser Asn
            100                 105                 110
```

Thr Thr Lys Pro Arg Phe Ser Pro Leu Val Ile Pro Leu Gly Ile Asp
        115                 120                 125

Thr Thr Ser Pro Thr Met Thr Leu Arg Pro Lys Leu Ile Asp Val Thr
    130                 135                 140

Pro Gly Ala Pro Asn Val Pro Ser Thr Pro Ser Val Pro Ser Pro Pro
145                 150                 155                 160

Ser Ala Thr Ala Ser Ala Pro Ala Lys Lys Thr Pro Pro Arg Leu Ala
                165                 170                 175

Phe Thr Gly Ala Ser Ile Leu Gly Leu Leu Ala Ile Ala Thr Ile Ser
            180                 185                 190

Thr Leu Ile Gly Ile Ala Leu Ile Arg Thr Arg Arg Ala Glu Asn Lys
        195                 200                 205

Gly

<210> SEQ ID NO 5
<211> LENGTH: 5
<212> TYPE: PRT
<213> ORGANISM: Corynebacterium diphtheriae
<220> FEATURE:
<221> NAME/KEY: MOD_RES
<222> LOCATION: (3)..(3)
<223> OTHER INFORMATION: Any amino acid

<400> SEQUENCE: 5

Leu Pro Xaa Thr Gly
1               5

<210> SEQ ID NO 6
<211> LENGTH: 4
<212> TYPE: PRT
<213> ORGANISM: Corynebacterium diphtheriae

<400> SEQUENCE: 6

Tyr Pro Lys Asn
1

<210> SEQ ID NO 7
<211> LENGTH: 4
<212> TYPE: PRT
<213> ORGANISM: Corynebacterium diphtheriae

<400> SEQUENCE: 7

Leu Pro Leu Thr
1

<210> SEQ ID NO 8
<211> LENGTH: 4
<212> TYPE: PRT
<213> ORGANISM: Corynebacterium diphtheriae
<220> FEATURE:
<221> NAME/KEY: MOD_RES
<222> LOCATION: (3)..(3)
<223> OTHER INFORMATION: Any amino acid

<400> SEQUENCE: 8

Leu Pro Xaa Thr
1

<210> SEQ ID NO 9
<211> LENGTH: 16
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 9

Lys Asn Ala Gly Phe Glu Leu Pro Leu Thr Gly Gly Ser Gly Arg Ile
1 5 10 15

<210> SEQ ID NO 10
<211> LENGTH: 8
<212> TYPE: PRT
<213> ORGANISM: Corynebacterium diphtheriae
<220> FEATURE:
<221> NAME/KEY: MOD_RES
<222> LOCATION: (3)..(3)
<223> OTHER INFORMATION: Tyr or Leu
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Ser or Thr

<400> SEQUENCE: 10

Thr Pro Xaa Xaa Ile Asn Xaa His
1 5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Asp Gly Trp Leu Gln Asp Val His Val Tyr Pro Lys His Gln Ala Leu
1 5 10 15

Ser

<210> SEQ ID NO 12
<211> LENGTH: 11
<212> TYPE: PRT
<213> ORGANISM: Corynebacterium diphtheriae
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 12

Trp Xaa Xaa Xaa Val Xaa Val Tyr Pro Lys His
1 5 10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Lys Asn Ala Gly Phe Glu Leu Pro Leu Thr Gly
1 5 10

<210> SEQ ID NO 14
<211> LENGTH: 3
<212> TYPE: PRT
<213> ORGANISM: Corynebacterium diphtheriae

<400> SEQUENCE: 14

Gly Pro Gly
1

<210> SEQ ID NO 15
<211> LENGTH: 10
<212> TYPE: PRT
<213> ORGANISM: Corynebacterium diphtheriae

<400> SEQUENCE: 15

Leu Pro Leu Thr Gly Gly Ser Gly Arg Ile
1 5 10

<210> SEQ ID NO 16
<211> LENGTH: 10
<212> TYPE: PRT
<213> ORGANISM: Corynebacterium diphtheriae
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 16

Trp Xaa Xaa Xaa Val Xaa Val Tyr Pro Lys
1 5 10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Lys Asn Ala Gly Phe Glu Leu Pro Ala Thr Gly Gly Ser Gly Arg Ile
1 5 10 15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Cys Asn Ala Gly Phe Glu Leu Pro Ala Thr Gly Gly Ser Arg Ile
1 5 10 15

<210> SEQ ID NO 19
<211> LENGTH: 4
<212> TYPE: PRT
<213> ORGANISM: Corynebacterium diphtheriae -continued

<400> SEQUENCE: 19

Cys Trp Ser Ser
1

<210> SEQ ID NO 20
<211> LENGTH: 31
<212> TYPE: PRT
<213> ORGANISM: Corynebacterium diphtheriae

<400> SEQUENCE: 20

```
Asp Pro Asn Lys Asp Gln Ile Thr Leu Ile Thr Cys Thr Pro Tyr Ala
1               5                   10                  15

Val Asn Ser His Arg Leu Leu Val Arg Ala His Arg Val Asp Leu
            20                  25                  30
```

<210> SEQ ID NO 21
<211> LENGTH: 31
<212> TYPE: PRT
<213> ORGANISM: Corynebacterium diphtheriae

<400> SEQUENCE: 21

```
Glu Gln Gly Lys Asp Tyr Ile Thr Leu Ile Thr Cys Thr Pro Tyr Gly
1               5                   10                  15

Ile Asn Thr His Arg Leu Met Val Arg Gly His Gln Val Pro Leu
            20                  25                  30
```

<210> SEQ ID NO 22
<211> LENGTH: 31
<212> TYPE: PRT
<213> ORGANISM: Corynebacterium diphtheriae

<400> SEQUENCE: 22

```
Thr Ser Asn Lys Asp Gln Val Thr Leu Ile Thr Cys Thr Pro Tyr Gly
1               5                   10                  15

Ile Asn Thr His Arg Leu Ile Ile Thr Ala Glu Arg Val Pro Met
            20                  25                  30
```

<210> SEQ ID NO 23
<211> LENGTH: 31
<212> TYPE: PRT
<213> ORGANISM: Corynebacterium diphtheriae

<400> SEQUENCE: 23

```
Gln Asp Asp Arg Asp Leu Val Thr Leu Val Thr Cys Thr Pro Leu Gly
1               5                   10                  15

Ile Asn Thr His Arg Ile Leu Val Thr Ala Glu Arg Ile Thr Pro
            20                  25                  30
```

<210> SEQ ID NO 24
<211> LENGTH: 31
<212> TYPE: PRT
<213> ORGANISM: Corynebacterium diphtheriae

<400> SEQUENCE: 24

```
Ile Pro Asp Arg Asp Leu Ile Thr Leu Val Thr Cys Thr Pro Tyr Gly
1               5                   10                  15

Ile Asn Thr His Arg Leu Leu Val Thr Ala Glu Arg Val Pro Met
            20                  25                  30
```

<210> SEQ ID NO 25
<211> LENGTH: 31

<212> TYPE: PRT
<213> ORGANISM: Lactobacillus rhamnosus

<400> SEQUENCE: 25

Val Pro Gly Gln Asp Leu Val Thr Leu Met Thr Cys Thr Pro Tyr Met
1 5 10 15

Ile Asn Ser His Arg Leu Leu Ile Thr Gly Arg Arg Ile Pro Tyr
20 25 30

<210> SEQ ID NO 26
<211> LENGTH: 31
<212> TYPE: PRT
<213> ORGANISM: Unknown
<220> FEATURE:
<223> OTHER INFORMATION: Description of Unknown:
faecium class C sortase 1 sequence

<400> SEQUENCE: 26

Ser Glu Gly Glu Asp Leu Val Thr Leu Leu Thr Cys Thr Pro Tyr Met
1 5 10 15

Ile Asn Thr His Arg Leu Leu Val Thr Gly His Arg Ile Pro Tyr
20 25 30

<210> SEQ ID NO 27
<211> LENGTH: 31
<212> TYPE: PRT
<213> ORGANISM: Unknown
<220> FEATURE:
<223> OTHER INFORMATION: Description of Unknown:
faecium class C sortase 2 sequence

<400> SEQUENCE: 27

Glu Lys Gly Gln Asp Phe Val Thr Leu Leu Thr Cys Thr Pro Tyr Met
1 5 10 15

Val Asn Ser His Arg Leu Leu Val Arg Gly His Arg Val Pro Tyr
20 25 30

<210> SEQ ID NO 28
<211> LENGTH: 31
<212> TYPE: PRT
<213> ORGANISM: Unknown
<220> FEATURE:
<223> OTHER INFORMATION: Description of Unknown:
SrtC1 sequence

<400> SEQUENCE: 28

Glu Glu Gly Lys Asp Leu Leu Thr Leu Val Thr Cys Thr Pro Leu Gly
1 5 10 15

Ile Asn Thr His Arg Ile Leu Leu Thr Gly Glu Arg Ile Tyr Pro
20 25 30

<210> SEQ ID NO 29
<211> LENGTH: 31
<212> TYPE: PRT
<213> ORGANISM: Actinomyces oris

<400> SEQUENCE: 29

Val Pro Gly Arg Asp Leu Val Thr Leu Ile Thr Cys Thr Pro Tyr Gly
1 5 10 15

Val Asn Ser His Arg Leu Leu Val Thr Gly Glu Arg Val Pro Met
20 25 30

<210> SEQ ID NO 30
<211> LENGTH: 31

<212> TYPE: PRT
<213> ORGANISM: Streptococcus pneumoniae

<400> SEQUENCE: 30

```
Gln His Gly Glu Asp Tyr Ala Thr Leu Leu Thr Cys Thr Pro Tyr Met
1               5                   10                  15

Ile Asn Ser His Arg Leu Leu Val Arg Gly Lys Arg Ile Pro Tyr
            20                  25                  30
```

<210> SEQ ID NO 31
<211> LENGTH: 31
<212> TYPE: PRT
<213> ORGANISM: Streptococcus agalactiae

<400> SEQUENCE: 31

```
Ile Gln Gly Glu Asp His Val Thr Leu Leu Thr Cys Thr Pro Tyr Met
1               5                   10                  15

Ile Asn Ser His Arg Leu Leu Val Arg Gly Lys Arg Ile Pro Tyr
            20                  25                  30
```

<210> SEQ ID NO 32
<211> LENGTH: 31
<212> TYPE: PRT
<213> ORGANISM: Streptococcus agalactiae

<400> SEQUENCE: 32

```
Val Asn Gly Lys Asp Tyr Ile Thr Leu Leu Thr Cys Thr Pro Tyr Met
1               5                   10                  15

Ile Asn Ser His Arg Leu Leu Val Lys Gly Glu Arg Ile Pro Tyr
            20                  25                  30
```

<210> SEQ ID NO 33
<211> LENGTH: 31
<212> TYPE: PRT
<213> ORGANISM: Bacillus cereus

<400> SEQUENCE: 33

```
Val Gln Asn Lys Asp Tyr Thr Thr Leu Ile Thr Cys Thr Pro Tyr Gly
1               5                   10                  15

Ile Asn Thr Asn Arg Leu Leu Val Arg Gly Glu Arg Val Glu Leu
            20                  25                  30
```

<210> SEQ ID NO 34
<211> LENGTH: 31
<212> TYPE: PRT
<213> ORGANISM: Ruminococcus albus

<400> SEQUENCE: 34

```
Ile Pro Asn Glu Asp Glu Val Thr Leu Met Thr Cys Thr Pro Tyr Gly
1               5                   10                  15

Ile Asn Thr His Arg Leu Leu Ile Arg Ala His Arg Ile Lys Ser
            20                  25                  30
```

<210> SEQ ID NO 35
<211> LENGTH: 35
<212> TYPE: PRT
<213> ORGANISM: Staphylococcus aureus

<400> SEQUENCE: 35

```
Gln Lys Gly Lys Asp Lys Gln Leu Thr Leu Ile Thr Cys Asp Asp Tyr
1               5                   10                  15
```

Asn Glu Lys Thr Gly Val Trp Glu Lys Arg Lys Ile Phe Val Ala Thr
20 25 30

Glu Val Lys
35

<210> SEQ ID NO 36
<211> LENGTH: 30
<212> TYPE: PRT
<213> ORGANISM: Streptococcus pyogenes

<400> SEQUENCE: 36

Lys His His Thr Lys Phe Val Ala Phe Ser Thr Cys Glu Asn Phe Ser
1 5 10 15

Thr Asp Asn Arg Val Ile Val Val Gly Thr Ile Gln Glu Ile
20 25 30

<210> SEQ ID NO 37
<211> LENGTH: 24
<212> TYPE: PRT
<213> ORGANISM: Clostridium perfringens

<400> SEQUENCE: 37

Lys Thr Met Thr Ile Val Thr Cys Thr Asn Arg Gly Lys Asp Arg Tyr
1 5 10 15

Ile Val Lys Ala Lys Leu Ile Gly
20

<210> SEQ ID NO 38
<211> LENGTH: 32
<212> TYPE: PRT
<213> ORGANISM: Streptomyces coelicolor

<400> SEQUENCE: 38

Phe Lys Gly Pro Gly Arg Tyr Ile Thr Leu Thr Thr Cys Thr Pro Glu
1 5 10 15

Phe Thr Ser Lys Tyr Arg Met Ile Val Trp Gly Lys Met Val Glu Glu
20 25 30

<210> SEQ ID NO 39
<211> LENGTH: 32
<212> TYPE: PRT
<213> ORGANISM: Corynebacterium diphtheriae

<400> SEQUENCE: 39

Asp Pro Gly Met Glu Gly Ile Met Thr Met Thr Thr Cys His Pro Gln
1 5 10 15

Phe Ser Asn Ala Glu Arg Met Ile Val His Ala Met Leu Thr Glu His
20 25 30

<210> SEQ ID NO 40
<211> LENGTH: 212
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Asn Asn Ala Arg Gln Ala Arg Val Ala Gln Ser Tyr Glu Asn Ser Tyr
1 5 10 15

Glu Val Asp Ser Pro Ala Val Arg Asp Ser Val Leu Glu Ala Ala Arg
20 25 30

```
Gln Tyr Asn Thr Ser Val Val Gly Phe Pro Ser Lys Asn Ser Gly Pro
        35                  40                  45

Tyr Leu Asp Tyr Leu Gln Gln Leu Asn Pro Gln Arg Ala Glu Arg Pro
    50                  55                  60

Val Ile Ala Ser Ile Ser Ile Pro Thr Ile Asp Ala His Leu Pro Ile
65                  70                  75                  80

Tyr His Gly Thr Asp Thr Ala Thr Leu Glu His Gly Leu Gly His Leu
                85                  90                  95

Tyr Gly Ser Ala Leu Pro Val Gly Gly Thr Gly Thr His Pro Val Ile
            100                 105                 110

Thr Gly His Ser Gly Leu Ala Asn Ala Thr Leu Phe Asp Asn Leu Glu
        115                 120                 125

Asp Val Lys Glu His Asp Pro Ile Tyr Ile Thr Val Gln Gly Glu Thr
    130                 135                 140

Leu Lys Tyr Glu Val Asp Ala Ile Asn Val Val Leu Pro Glu Asp Thr
145                 150                 155                 160

Lys Leu Leu Ala Pro Asp Pro Asn Lys Asp Gln Ile Thr Leu Ile Thr
                165                 170                 175

Cys Thr Pro Tyr Ala Val Asn Ser His Arg Leu Leu Val Arg Ala His
            180                 185                 190

Arg Val Asp Leu Asp Pro Asn Asp Pro Asn Leu Thr Gln Thr Gly Thr
        195                 200                 205

Lys Ile Trp Gln
    210


<210> SEQ ID NO 41
<211> LENGTH: 289
<212> TYPE: PRT
<213> ORGANISM: Corynebacterium diphtheriae

<400> SEQUENCE: 41

Met Arg His Arg Ala Gly Glu His Arg Asn Val Phe Ala Ile Leu Ala
1               5                   10                  15

Phe Val Ile Ala Ile Val Ser Val Gly Phe Leu Leu Tyr Pro Val Ala
            20                  25                  30

Ala Thr Ala Trp Asn Asn Ala Arg Gln Ala Arg Val Ala Gln Ser Tyr
        35                  40                  45

Glu Asn Ser Tyr Glu Val Asp Ser Pro Ala Val Arg Asp Ser Val Leu
    50                  55                  60

Glu Ala Ala Arg Gln Tyr Asn Thr Ser Val Val Gly Phe Pro Ile Leu
65                  70                  75                  80

Asp Pro Trp Leu Asn Arg Ala Ser Lys Asn Ser Gly Pro Tyr Leu Asp
                85                  90                  95

Tyr Leu Gln Gln Leu Asn Pro Gln Arg Ala Glu Arg Pro Val Ile Ala
            100                 105                 110

Ser Ile Ser Ile Pro Thr Ile Asp Ala His Leu Pro Ile Tyr His Gly
        115                 120                 125

Thr Asp Thr Ala Thr Leu Glu His Gly Leu Gly His Leu Tyr Gly Ser
    130                 135                 140

Ala Leu Pro Val Gly Gly Thr Gly Thr His Pro Val Ile Thr Gly His
145                 150                 155                 160

Ser Gly Leu Ala Asn Ala Thr Leu Phe Asp Asn Leu Glu Asp Val Lys
                165                 170                 175
```

-continued

```
Glu His Asp Pro Ile Tyr Ile Thr Val Gln Gly Glu Thr Leu Lys Tyr
            180                 185                 190

Glu Val Asp Ala Ile Asn Val Val Leu Pro Glu Asp Thr Lys Leu Leu
        195                 200                 205

Ala Pro Asp Pro Asn Lys Asp Gln Ile Thr Leu Ile Thr Cys Thr Pro
    210                 215                 220

Tyr Ala Val Asn Ser His Arg Leu Leu Val Arg Ala His Arg Val Asp
225                 230                 235                 240

Leu Asp Pro Asn Asp Pro Asn Leu Thr Gln Thr Gly Thr Lys Ile Trp
                245                 250                 255

Gln Pro Trp Met Leu Trp Thr Ala Ala Leu Ala Leu Thr Ala Ile Ala
            260                 265                 270

Ile Ile Ile Thr Leu Val Leu Arg Arg Lys Arg Thr Thr Thr His Glu
        275                 280                 285

Lys
```